United States Patent
Aharoni et al.

(10) Patent No.: US 9,850,294 B2
(45) Date of Patent: Dec. 26, 2017

(54) IL-17R-ECD MUTANTS AND METHODS OF USING SAME

(71) Applicant: THE NATIONAL INSTITUTE FOR BIOTECHNOLOGY IN THE NEGEV, LTD., Beer Sheva (IL)

(72) Inventors: Amir Aharoni, Beit Kama (IL); Marianna Zaretzky, Beer Sheva (IL)

(73) Assignee: THE NATIONAL INSTITUTE FOR BIOTECHNOLOGY IN THE NEGEV, LTD., Beer Sheva (IL)

( * ) Notice: Subject to any disclaimer, the term of this patent is extended or adjusted under 35 U.S.C. 154(b) by 0 days.

(21) Appl. No.: 15/205,074

(22) Filed: Jul. 8, 2016

(65) Prior Publication Data
US 2016/0376343 A1 Dec. 29, 2016

Related U.S. Application Data

(63) Continuation of application No. 14/232,921, filed as application No. PCT/IB2012/001400 on Jul. 18, 2012, now Pat. No. 9,416,168.

(60) Provisional application No. 61/509,236, filed on Jul. 19, 2011.

(51) Int. Cl.
| | | |
|---|---|---|
| *A61K 38/17* | (2006.01) | |
| *C07K 14/715* | (2006.01) | |
| *C07K 14/54* | (2006.01) | |
| *A61K 45/06* | (2006.01) | |
| *A61K 38/20* | (2006.01) | |
| *A61K 38/00* | (2006.01) | |

(52) U.S. Cl.
CPC ...... *C07K 14/7155* (2013.01); *A61K 38/1793* (2013.01); *A61K 38/2006* (2013.01); *A61K 45/06* (2013.01); *C07K 14/54* (2013.01); *A61K 38/00* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos |
| 4,501,728 A | 2/1985 | Geho |
| 4,837,028 A | 6/1989 | Allen |
| 5,019,369 A | 5/1991 | Presant |
| 7,217,412 B2 | 5/2007 | Chen et al. |
| 2007/0197441 A1 | 8/2007 | Rixon et al. |

FOREIGN PATENT DOCUMENTS

| | | |
|---|---|---|
| WO | 2008054603 A2 | 5/2008 |
| WO | 2011046958 A1 | 4/2011 |

OTHER PUBLICATIONS

Aggarwal, S et al. Interleukin-23 Promotes a Distinct CD4 T Cell Activation State Characterized by the Production of Interleukin-17. Journal of Biological Chemistry 278, 1910-1914 (2003).
Kolls, J.K. Interleukin-17 family members and inflammation. Immunity 21, 467-476 (2004).
Iwakura, Y. The IL-23/IL-17 axis in inflammation. The Journal of Clinical Investigation 116, 1218-1222 (2006).
Nakae, S. et al. Antigen-specific T cell sensitization is impaired in IL-17-deficient mice, causing suppression of allergic cellular and humoral responses. Immunity 17, 375-387 (2002).
Aggarwal, S. Journal of Leukocyte Biology 71, 1-8 (2002).
Toy, D. et al. The Journal of Immunology 111, 36-39 (2006).
Kramer, J.M. et al. The Journal of Immunology 179, 6379-6383 (2007).
Gaffen, S.L. Structure and signalling in the IL-17 receptor superfamily. Nat Rev Immunol 9, 556-567 (2009).
Ely, L.K. Structural basis of receptor sharing by interleukin 17 cytokines. Nat Immunol 10, 1245-1251 (2009).
European Search Report received in a counterpart foreign application—EP2734541—entitled Novel IL-17R-ECD Mutants, dated Jan. 20, 2016. 11 pages.
Zaretsky Mariana et al., "Directed evolution of a soluble human IL-17A receptor for the inhibition of psoriasis plaque formation in a mouse model.", Chem Biol. Feb. 21, 2013;20(2):202-11. doi: 10.1016/j.chembiol.2012.11.012. 10 pages.

*Primary Examiner* — Dong Jiang
(74) *Attorney, Agent, or Firm* — Roach Brown McCarthy & Gruber, P.C.; Kevin D. McCarthy

(57) ABSTRACT

A protein comprising an amino acid sequence having at least 97% homology to SEQ ID NO: 1. The amino acid sequence comprises valine at position 60, glycine at position 123 and lysine at position 109 and the protein binds hIL17A.

20 Claims, 13 Drawing Sheets

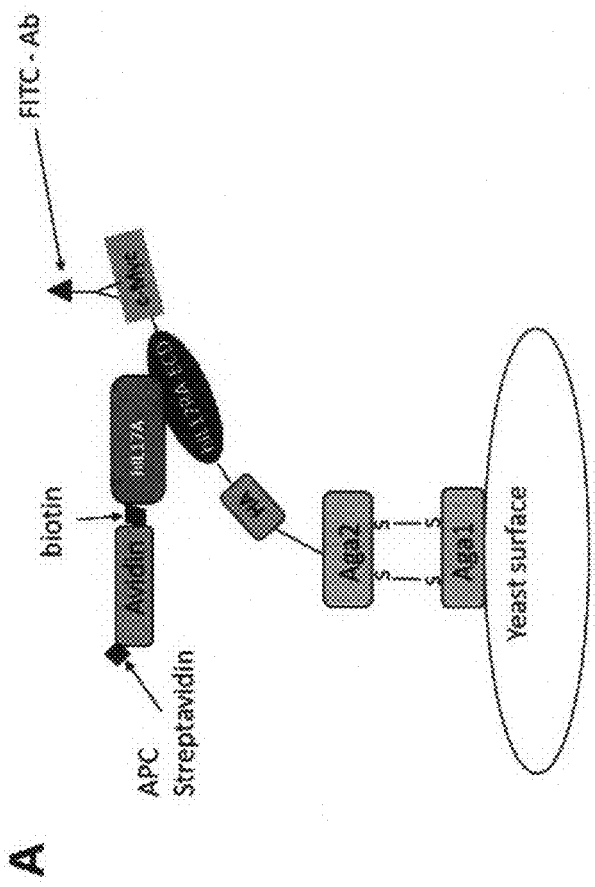
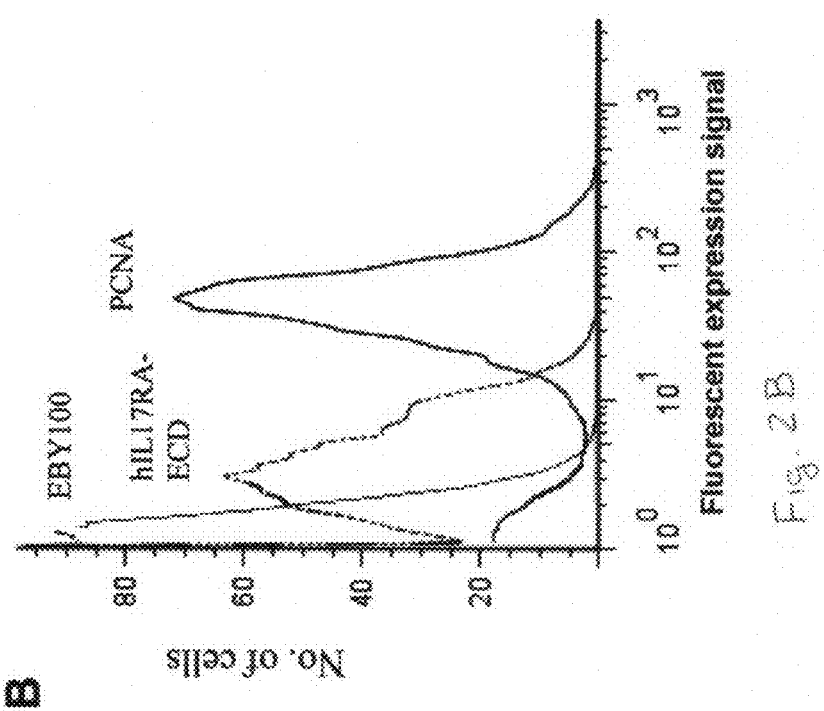
Fig. 2A
Fig. 2B

SEQUENCE LISTING

<160> NUMBER OF SEQ ID NOS: 76

<210> SEQ ID NO 1
<211> LENGTH: 289
<212> TYPE: PRT
<213> ORGANISM: Artificial Sequence
<220> FEATURE:
<223> OTHER INFORMATION: Artifical Construct of Wild Type IL-17R-ECD

<400> SEQUENCE: 1

```
Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Phe Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Arg Arg Trp Arg
            100                 105                 110

Phe Thr Phe Ser His Phe Val Val Asp Pro Asp Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220
```

```
Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
            245                 250                 255

Ser Ser Cys Leu Asn Asp Cys Leu Arg His Ser Ala Thr Val Ser Cys
        260                 265                 270

Pro Glu Met Pro Asp Thr Pro Glu Pro Ile Pro Asp Tyr Met Pro Leu
    275                 280                 285

Trp

<210> SEQ ID NO 2
<211> LENGTH: 289
<212> TYPE: PRT
<213> ORGANISM: Artificial Sequence
<220> FEATURE:
<223> OTHER INFORMATION: Artificial variant of IL-17R-ECD MUTANT

<400> SEQUENCE: 2

Ser Leu Arg Leu Leu Asp His Arg Ala Leu Val Cys Ser Gln Glu Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asn Leu Gln Ile Gln
        35                  40                  45

Leu His Phe Ala His Thr Gln Gln Gly Asp Leu Leu Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
                100                 105                 110

Phe Thr Phe Ser His Phe Val Val Asp Pro Asp Gln Glu Tyr Glu Val
            115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Ser
225                 230                 235                 240

Asn Leu Lys Gly Cys Cys Arg His Gln Val Gln Ile Gln Pro Phe Phe
            245                 250                 255

Ser Ser Cys Leu Asn Asp Cys Leu Arg His Ser Ala Thr Val Ser Cys
        260                 265                 270

Pro Glu Met Pro Asp Thr Pro Glu Pro Ile Pro Asp Tyr Met Pro Leu
    275                 280                 285

Trp
```

<210> SEQ ID NO 3
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 3

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asn Leu Gln Ile Gln
        35                  40                  45

Leu His Phe Ala His Thr Gln Gln Gly Asp Leu Phe Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Le

```
Leu Asn Cys Thr Val Lys Asn Ser Thr Cys Leu Asp Asp Ser Trp Ile
             20                  25                  30

His Pro Arg Asn Leu Thr Pro Ser Pro Lys Asp Leu Gln Ile Gln
         35                  40                  45

Leu His Phe Ala His Thr Gln Gln Gly Asp Leu Phe Pro Val Ala His
     50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                 85                  90                  95

Arg Phe Glu Phe Leu Ser Lys Leu Arg His His Lys Arg Trp Arg
            100                 105                 110

Phe Thr Phe Ser His Phe Val Val Asp Pro Gly Gln Glu Tyr Glu Val
            115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu Asp Ala Arg Met Lys
145                 150                 155                 160

Val Thr Thr Pro Cys Met Ser Gly Ser Leu Trp Asp Pro Asn Ile
                165                 170                 175

Thr Val Glu Thr Leu Glu Ala His Gln Leu Arg Val Ser Phe Thr Leu
                180                 185                 190

Trp Asn Glu Ser Thr His Tyr Gln Ile Leu Leu Thr Ser Phe Pro His
            195                 200                 205

Met Glu Asn His Ser Cys Phe Glu His Met His His Ile Pro Ala Pro
            210                 215                 220

Arg Pro Glu Glu Phe His Gln Arg Ser Asn Val Thr Leu Thr Leu Arg
225                 230                 235                 240

Asn Leu Lys Trp Cys Cys Arg His Gln Val Gln Ile Gln Pro Phe Phe
                245                 250                 255

Ser Ser Cys Leu Asn Asp Cys Leu Arg His Ser Val Thr Val Ser Cys
            260                 265                 270

Pro Glu Met Pro Asp Thr Pro Glu Pro Ile Pro Asp Tyr Met Pro Leu
            275                 280                 285

Trp

<210> SEQ ID NO 5
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 5

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
             20                  25                  30

His Pro Arg Asn Leu Thr Pro Ser Pro Lys Asp Ile Gln Ile Gln
         35                  40                  45

Leu His Phe Ala His Thr Gln Gln Gly Asp Leu Leu Pro Val Ala His
     50                  55                  60

Ile Glu Trp Thr Pro Gln Thr Asp Ala Ser Ile Leu Tyr Leu Glu Gly
65                  70                  75                  80
```

```
Ala Glu Leu Ser Val Leu Gln Leu Asn Thr Asn Glu Arg Leu Cys Val
             85                  90                  95

Arg Phe Glu Phe Leu Ser Lys Leu Arg His His His Arg Arg Trp Arg
            100                 105                 110

Phe Thr Phe Ser His Phe Val Val Asp Pro Asp Gln Glu Tyr Glu Val
            115                 120                 125

Thr Val His His Leu Pro Lys Pro Ile Pro Asp Gly Asp Pro Asn His
        130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp

<210> SEQ ID NO 6
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 6

Ser Leu Arg Leu Leu Asp His Arg Ala Leu Val Cys Ser Gln Pro Gly
1               5                  10                  15

Leu Asn Cys Thr Val Lys Asn Ser Thr Cys Leu Asp Asp Ser Trp Ile
                20                  25                  30

His Pro Arg Asn Leu Thr Pro Ser Ser Pro Lys Asn Leu Gln Ile Gln

```
            145                 150                 155                 160
Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
                180                 185                 190

Trp Asn Glu Ser Thr His Tyr Gln Ile Leu Leu Thr Ser Phe Pro His
                195                 200                 205

Met Glu Asn His Ser Cys Phe Glu His Met His His Ile Pro Ala Pro
                210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro Glu Met Pro Asp Thr Pro Glu Pro Ile Pro Asp Tyr Met Pro Leu
                275                 280                 285

Trp

<210> SEQ ID NO 7
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 7

Ser Leu Arg Leu Leu Asp His Arg Ala Leu Val Cys Ser Gln Glu Gly
1               5                   10                  15

Leu Asn Cys Thr Val Lys Asn Ser Thr Cys Leu Asp Asp Ser Trp Ile
                20                  25                  30

His Pro Arg Asn Leu Thr Pro Ser Ser Pro Lys Asp Leu Gln Ile Gln
            35                  40                  45

Leu His Phe Ala His Thr Gln Gln Gly Asp Leu Leu Pro Val Ala His
        50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
                100                 105                 110

Phe Thr Phe Ser His Phe Val Val Asp Pro Gly Gln Glu Tyr Glu Val
                115                 120                 125

Thr Val His His Leu Pro Lys Pro Ile Pro Asp Gly Asp Pro Asn His
            130                 135                 140

Gln Ser Lys Asn Phe Leu Val Pro Asp Cys Glu His Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
                180                 185                 190

Trp Asn Glu Ser Thr His Tyr Gln Ile Leu Leu Thr Ser Phe Pro His
                195                 200                 205

Met Glu Asn His Ser Cys Phe Glu His Met His His Ile Pro Ala Pro
                210                 215                 220
```

```
Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp

<210> SEQ ID NO 8
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 8

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Val Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
            100                 105                 110

Phe Thr Phe Ser His Phe Val Val Asp Pro Asp Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285
```

Trp

<210> SEQ ID NO 9
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 9

```
Ser Leu Arg Leu Leu Asp His Arg Ala Leu Val Cys Ser Gln Glu Gly
 1               5                  10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Phe Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
            100                 105                 110

Phe Thr Phe Ser His Phe Val Val Asp Pro Asp Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp
```

<210> SEQ ID NO 10
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 10

```
Ser Leu Arg Leu Leu Asp His Arg Ala Pro Val Cys Ser Gln Glu Gly
```

```
              1               5                  10                 15
            Leu Asn Cys Thr Val Lys Asn Ser Thr Cys Leu Asp Asp Ser Trp Ile
                             20                 25                 30
            His Pro Arg Asn Leu Thr Pro Ser Pro Lys Asn Leu Gln Ile Gln
                         35                 40                 45
            Leu His Phe Ala His Thr Gln Gln Gly Asp Leu Leu Pro Val Ala His
                50                 55                 60
            Ile Glu Trp Thr Leu Gln Thr Asp Ala Ser Ile Leu Tyr Leu Glu Gly
            65                 70                 75                 80
            Ala Glu Leu Ser Val Leu Gln Leu Asn Thr Asn Glu Arg Leu Cys Val
                             85                 90                 95
            Lys Phe Glu Phe Leu Ser Lys Leu Arg His His Lys Arg Trp Arg
                         100                105                110
            Phe Thr Phe Ser His Phe Val Val Asp Pro Asp Gln Glu Tyr Glu Val
                         115                120                125
            Thr Val His His Leu Pro Lys Pro Ile Pro Asp Gly Asp Pro Asn His
                         130                135                140
            Gln Ser Lys Asn Phe Leu Val Pro Asp Cys Glu His Ala Arg Met Lys
            145                150                155                160
            Val Thr Thr Pro Cys Met Ser Ser Gly Ser Leu Trp Asp Pro Asn Ile
                             165                170                175
            Thr Val Glu Thr Leu Glu Ala His Gln Leu Arg Val Ser Phe Thr Leu
                         180                185                190
            Trp Asn Glu Ser Thr His Tyr Gln Ile Leu Leu Thr Ser Phe Pro His
                         195                200                205
            Met Glu Asn His Ser Cys Phe Glu His Met His His Ile Pro Ala Pro
                         210                215                220
            Arg Pro Glu Glu Phe His Gln Arg Ser Asn Val Thr Leu Thr Leu Arg
            225                230                235                240
            Asn Leu Lys Gly Cys Cys Arg His Gln Val Gln Ile Gln Pro Phe Phe
                             245                250                255
            Ser Ser Cys Leu Asn Asp Cys Leu Arg His Ser Ala Thr Val Ser Cys
                         260                265                270
            Pro Glu Met Pro Asp Thr Pro Glu Pro Ile Pro Asp Tyr Met Pro Leu
                         275                280                285
            Trp

<210> SEQ ID NO 11
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 11

Ser Leu Arg Leu Leu Asp His Arg Ala Pro Val Cys Ser Gln Pro Gly
            1               5                  10                 15
            Leu Asn Cys Thr Val Lys Asn Ser Thr Cys Leu Asp Asp Ser Trp Ile
                             20                 25                 30
            His Pro Arg Asn Leu Thr Pro Ser Ser Pro Lys Asp Leu Gln Ile Gln
                         35                 40                 45
            Leu His Phe Ala His Thr Gln Gln Gly Asp Leu Val Pro Val Ala His
                50                 55                 60
            Ile Glu Trp Thr Leu Gln Thr Asp Ala Ser Ile Leu Tyr Leu Glu Gly
            65                 70                 75                 80
```

Ala Glu Leu Ser Val Leu Gln Leu Asn Thr Asn Glu Arg Leu Cys Val
            85                  90                  95

Arg Phe Glu Phe Leu Ser Lys Leu Arg His His Lys Arg Trp Arg
            100                 105                 110

Phe Thr Phe Ser His Phe Val Val Asp Pro Gly Gln Glu Tyr Glu Val
            115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
            165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
            195                 200                 205

Met Glu Asn His Ser Cys Phe Glu His Met His His Ile Pro Ala Pro
            210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
            245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
            275                 280                 285

Trp

<210> SEQ ID NO 12
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 12

Ser Leu Arg Leu Leu Asp His Arg Ala Leu Val Cys Ser Gln Glu Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
            35                  40                  45

Leu His Phe Ala His Thr Gln Gln Gly Asp Leu Phe Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
            85                  90                  95

Arg Phe Glu Phe Leu Ser Lys Leu Arg His His His Lys Arg Trp Arg
            100                 105                 110

Phe Thr Phe Ser His Phe Val Val Asp Pro Asp Arg Glu Tyr Glu Val
            115                 120                 125

Thr Val His His Leu Pro Lys Pro Ile Pro Asp Gly Asp Pro Asn His
    130                 135                 140

```
Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
            165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
            195                 200                 205

Met Glu Asn His Ser Cys Phe Glu His Met His His Ile Pro Ala Pro
            210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
            245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
            275                 280                 285

Trp

<210> SEQ ID NO 13
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 13

Ser Leu Arg Leu Leu Asp His Arg Ala Pro Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
            35                  40                  45

Leu His Phe Ala His Thr Gln Gln Gly Asp Leu Phe Pro Val Ala His
    50                  55                  60

Ile Glu Trp Thr Leu Gln Thr Asp Ala Ser Ile Leu Tyr Leu Glu Gly
65              70                  75                  80

Ala Glu Leu Ser Val Leu Gln Leu Asn Thr Asn Glu Arg Leu Cys Val
            85                  90                  95

Arg Phe Glu Phe Leu Ser Lys Leu Arg His His His Arg Arg Trp Arg
            100                 105                 110

Phe Thr Phe Ser Arg Phe Val Val Asp Pro Asp Gln Glu Tyr Glu Val
            115                 120                 125

Thr Val His His Leu Pro Lys Pro Ile Pro Asp Gly Asp Pro Asn His
            130                 135                 140

Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
            165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
            195                 200                 205

Met Glu Asn His Ser Cys Phe Glu His Met His His Ile Pro Ala Pro
```

```
                210                 215                 220
Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro Glu Met Pro Asp Thr Pro Glu Pro Ile Pro Asp Tyr Met Pro Leu
                275                 280                 285

Trp

<210> SEQ ID NO 14
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 14

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
                20                  25                  30

His Pro Arg Asn Leu Thr Pro Ser Ser Pro Lys Asp Leu Gln Ile Gln
                35                  40                  45

Leu His Phe Ala His Thr Gln Gln Gly Asp Leu Phe Pro Val Ala His
            50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Lys Phe Glu Phe Leu Ser Lys Leu Arg His His His Arg Arg Trp Arg
                100                 105                 110

Phe Thr Phe Ser His Phe Val Val Asp Pro Asp Gln Glu Tyr Glu Val
                115                 120                 125

Thr Val His His Leu Pro Lys Pro Ile Pro Asp Gly Asp Pro Asn His
            130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
                180                 185                 190

Trp Asp Glu Ser Thr His Tyr Gln Ile Leu Leu Thr Ser Phe Pro His
            195                 200                 205

Met Glu Asn His Ser Cys Phe Glu His Met His His Ile Pro Ala Pro
                210                 215                 220

Arg Pro Glu Glu Phe His Gln Arg Ser Asn Val Thr Leu Thr Leu Arg
225                 230                 235                 240

Asn Leu Lys Trp Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro Glu Met Pro Asp Thr Pro Glu Pro Ile Pro Asp Tyr Met Pro Leu
                275                 280                 285
```

Trp

```
<210> SEQ ID NO 15
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 15
```

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Val Gln Ile Gln
        35                  40                  45

Leu His Phe Ala His Thr Gln His Gly Asp Leu Phe Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
            100                 105                 110

Phe Thr Phe Ser His Phe Val Val Asp Pro Asp Gln Glu Tyr Glu Val
        115                 120                 125

Thr Val His His Leu Pro Lys Pro Ile Pro Asp Arg Asp Pro Asn His
    130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His His Val Gln Ile Gln Pro Phe Phe
                245                 250                 255

Ser Ser Cys Leu Asn Asp Cys Leu Arg His Ser Val Thr Val Ser Cys
            260                 265                 270

Pro Glu Met Pro Asp Thr Pro Glu Pro Ile Pro Asp Tyr Met Pro Leu
        275                 280                 285

Trp

```
<210> SEQ ID NO 16
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 16
```

```
Ser Leu Arg Leu Leu Asp His Arg Ala Leu Val Cys Ser Gln Pro Gly
1               5                   10                  15
Leu Asn Cys Thr Val Lys Asn Ser Thr Cys Leu Asp Asp Ser Trp Ile
            20                  25                  30
His Pro Arg Asn Leu Thr Pro Ser Ser Pro Lys Asp Val Gln Ile Gln
        35                  40                  45
Leu His Phe Ala His Thr Gln Gln Gly Asp Leu Phe Pro Val Ala His
    50                  55                  60
Ile Glu Trp Thr Leu Gln Thr Asp Ala Ser Ile Leu Tyr Leu Glu Gly
65                  70                  75                  80
Ala Glu Leu Ser Val Leu Gln Leu Asn Thr Asn Glu Arg Leu Cys Val
                85                  90                  95
Arg Phe Glu Ile Leu Ser Lys Leu Arg His His Arg Arg Trp Arg
            100                 105                 110
Phe Thr Phe Ser His Phe Val Val Asp Pro Gly Gln Glu Tyr Glu Val
            115                 120                 125
Thr Val His His Leu Pro Lys Pro Ile Pro Asp Gly Asp Pro Asn His
    130                 135                 140
Gln Ser Lys Asn Phe Leu Val Pro Asp Cys Glu His Ala Arg Met Lys
145                 150                 155                 160
Val Thr Thr Pro Cys Met Ser Ser Gly Ser Leu Trp Asp Pro Asn Ile
                165                 170                 175
Thr Val Glu Thr Leu Glu Ala His Gln Leu Arg Val Ser Phe Thr Leu
            180                 185                 190
Trp Asn Glu Ser Thr His Tyr Gln Ile Leu Leu Thr Ser Phe Pro His
        195                 200                 205
Met Glu Asn His Ser Cys Phe Glu His Met His His Ile Pro Ala Pro
    210                 215                 220
Arg Pro Glu Glu Phe His Gln Arg Ser Asn Val Thr Leu Thr Leu Arg
225                 230                 235                 240
Asn Leu Lys Gly Cys Cys Arg His Gln Val Gln Ile Gln Pro Phe Phe
                245                 250                 255
Ser Ser Cys Leu Asn Asp Cys Leu Arg His Ser Val Thr Val Ser Cys
            260                 265                 270
Pro Glu Met Pro Asp Thr Pro Glu Pro Ile Pro Asp Tyr Met Pro Leu
        275                 280                 285
Trp

<210> SEQ ID NO 17
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 17

Ser Leu Arg Leu Leu Asp His Arg Ala Pro Val Cys Ser Gln Glu Gly
1               5                   10                  15
Leu Asn Cys Thr Val Lys Asn Ser Thr Cys Leu Asp Asp Ser Trp Ile
            20                  25                  30
His Pro Arg Asn Leu Thr Pro Ser Ser Pro Lys Asp Leu Gln Ile Gln
        35                  40                  45
Leu His Phe Ala His Thr Gln Gln Gly Asp Leu Phe Pro Val Ala His
    50                  55                  60
Ile Glu Trp Thr Leu Gln Thr Asp Ala Ser Ile Leu Tyr Leu Glu Gly
```

```
                        65                  70                  75                  80
Ala Glu Leu Ser Val Leu Gln Leu Asn Thr Asn Glu Arg Leu Cys Val
                    85                  90                  95

Arg Phe Glu Phe Leu Ser Lys Leu Arg His His Lys Arg Trp Arg
                100                 105                 110

Phe Thr Phe Ser His Phe Val Val Asp Pro Asp Gln Glu Tyr Glu Val
            115                 120                 125

Thr Val His His Leu Pro Lys Pro Ile Pro Asp Gly Asp Pro Asn His
        130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp

<210> SEQ ID NO 18
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 18

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
                20                  25                  30

His Pro Arg Asn Leu Thr Pro Ser Ser Pro Lys Asp Leu Gln Ile Gln
            35                  40                  45

Leu His Phe Ala His Thr Gln Gln Gly Asp Leu Phe Pro Val Ala His
        50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Glu Leu Arg His His Arg Arg Trp Arg
                100                 105                 110

Phe Thr Phe Ser His Phe Val Val Asp Pro Gly Gln Glu Tyr Glu Val
            115                 120                 125

Thr Val His His Leu Pro Lys Pro Ile Pro Asp Gly Asp Pro Asn His
        130                 135                 140
```

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
            165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
            195                 200                 205

Met Glu Asn His Ser Cys Phe Glu His Met His His Ile Pro Ala Pro
210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
            275                 280                 285

Trp

<210> SEQ ID NO 19
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 19

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
            35                  40                  45

Leu His Phe Ala His Thr Gln Gln Gly Asp Leu Phe Pro Val Ala His
        50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asp Thr Asn Glu Arg Leu Cys Val
                85                  90                  95

Arg Phe Glu Phe Leu Ser Lys Leu Arg His His His Arg Arg Trp Arg
            100                 105                 110

Phe Thr Phe Ser His Phe Val Val Asp Pro Gly Gln Glu Tyr Glu Val
            115                 120                 125

Thr Val His His Leu Pro Lys Pro Ile Pro Asp Gly Asp Pro Asn His
            130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
            165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
            195                 200                 205

```
Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp

<210> SEQ ID NO 20
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 20

Ser Leu Arg Leu Leu Asp His Gln Ala Leu Val Cys Ser Gln Glu Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Ile Gln Ile Gln
        35                  40                  45

Leu His Phe Ala His Thr Gln Gln Gly Asp Leu Leu Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Arg Arg Trp Arg
            100                 105                 110

Phe Thr Phe Ser His Phe Val Val Asp Pro Asp Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
```

<210> SEQ ID NO 21
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 21

```
Ser Leu Arg Leu Leu Asp His Arg Ala Pro Val Cys Ser Gln Glu Gly
1               5                   10                  15
Leu Asn Cys Thr Val Lys Asn Ser Thr Cys Leu Asp Asp Ser Trp Ile
            20                  25                  30
His Pro Arg Asn Leu Thr Pro Ser Pro Lys Asp Val Gln Ile Gln
        35                  40                  45
Leu His Phe Ala His Thr Gln Gln Gly Asp Leu Val Pro Val Ala His
    50                  55                  60
Ile Glu Trp Thr Leu Gln Thr Asp Ala Ser Ile Leu Tyr Leu Glu Gly
65                  70                  75                  80
Ala Glu Leu Ser Val Leu Gln Leu Asn Thr Asn Glu Arg Leu Cys Val
                85                  90                  95
Arg Phe Glu Phe Leu Ser Lys Leu Arg His His His Arg Arg Trp Arg
            100                 105                 110
Phe Thr Phe Ser His Phe Val Val Asp Pro Asp Arg Glu Tyr Glu Val
        115                 120                 125
Thr Val His His Leu Pro Lys Pro Ile Pro Asp Gly Asp Pro Asn His
    130                 135                 140
Gln Ser Lys Asn Phe Leu Val Pro Asp Cys Glu His Pro Arg Met Lys
145                 150                 155                 160
Val Thr Thr Pro Cys Met Ser Ser Gly Ser Leu Trp Asp Pro Asn Ile
                165                 170                 175
Thr Val Glu Thr Leu Glu Ala His Gln Leu Arg Val Ser Phe Thr Leu
            180                 185                 190
Trp Asn Glu Ser Thr His Tyr Gln Ile Leu Leu Thr Ser Phe Pro His
        195                 200                 205
Met Glu Asn His Ser Cys Phe Glu His Met His His Ile Pro Ala Pro
    210                 215                 220
Arg Pro Glu Glu Phe His Gln Arg Ser Asn Val Thr Leu Thr Leu Arg
225                 230                 235                 240
Asn Leu Lys Gly Cys Cys Arg His Gln Val Gln Ile Gln Pro Phe Phe
                245                 250                 255
Ser Ser Cys Leu Asn Asp Cys Leu Arg His Ser Ala Thr Val Ser Cys
            260                 265                 270
Pro Glu Met Pro Asp Thr Pro Glu Pro Ile Pro Asp Tyr Met Pro Leu
        275                 280                 285
Trp
```

<210> SEQ ID NO 22
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 22

```
Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Leu Pro Val Ala His
    50                  55                  60

Ile Glu Trp Thr Leu Gln Thr Asp Ala Ser Ile Leu Tyr Leu Glu Gly
65              70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
            100                 105                 110

Phe Thr Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Lys Ala His Gln Leu Arg Val Ser Phe Thr Leu
            180                 185                 190

Trp Asn Glu Ser Thr His Tyr Gln Ile Leu Leu Ile Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp

<210> SEQ ID NO 23
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 23

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Val Pro Val Ala His
    50                  55                  60
```

```
Ile Glu Trp Thr Leu Gln Thr Asp Ala Ser Ile Leu Tyr Leu Glu Gly
 65                  70                  75                  80

Ala Glu Leu Ser Val Leu Gln Leu Asn Thr Asn Glu Arg Leu Cys Val
                 85                  90                  95

Arg Phe Glu Phe Leu Ser Lys Leu Arg His His His Arg Arg Trp Arg
            100                 105                 110

Phe Thr Phe Ser His Phe Val Val Asp Pro Asp Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu Asp Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp
```

<210> SEQ ID NO 24
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 24

```
Ser Leu Arg Leu Leu Asp His Arg Ala Leu Val Cys Ser Gln Pro Gly
  1               5                  10                  15

Leu Asn Cys Thr Val Lys Asn Ser Thr Cys Leu Asp Asp Ser Trp Ile
                 20                  25                  30

His Pro Arg Asn Leu Thr Pro Ser Ser Pro Lys Asp Leu Gln Ile Gln
             35                  40                  45

Leu His Phe Ala His Thr Gln Gln Gly Asp Leu Val Pro Val Ala His
         50                  55                  60

Ile Glu Trp Thr Leu Gln Thr Asp Ala Ser Thr Leu Tyr Leu Glu Gly
 65                  70                  75                  80

Ala Glu Leu Ser Val Leu Gln Leu Asn Thr Asn Glu Arg Leu Cys Val
                 85                  90                  95

Arg Phe Glu Phe Leu Ser Lys Leu Arg His His His Lys Arg Trp Arg
            100                 105                 110

Phe Thr Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
```

```
                130                 135                 140
Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
                180                 185                 190

Trp Asn Glu Ser Thr His Tyr Gln Ile Leu Leu Thr Ser Phe Pro His
                195                 200                 205

Thr Glu Asn His Ser Cys Phe Glu His Met His His Ile Pro Ala Pro
                210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro Glu Met Pro Asp Thr Pro Glu Pro Ile Pro Asp Tyr Met Pro Leu
                275                 280                 285

Trp

<210> SEQ ID NO 25
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 25

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
                20                  25                  30

His Pro Arg Asn Leu Thr Pro Ser Ser Pro Lys Asp Leu Gln Ile Gln
                35                  40                  45

Leu His Phe Ala His Thr Gln Gln Gly Asp Leu Val Pro Val Ala His
        50                  55                  60

Ile Glu Trp Thr Leu Gln Thr Asp Ala Ser Ile Leu Tyr Leu Lys Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
                100                 105                 110

Phe Thr Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
        130                 135                 140

Gln Ser Lys Asn Phe Leu Val Pro Asp Cys Gl

```
Met Glu Asn His Ser Cys Phe Glu His Met His Ile Pro Ala Pro
        210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro Glu Met Pro Asp Thr Pro Glu Pro Ile Pro Asp Tyr Met Pro Leu
                275                 280                 285

Trp

<210> SEQ ID NO 26
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 26

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
                20                  25                  30

His Pro Arg Asn Leu Thr Pro Ser Ser Pro Lys Asp Leu Gln Ile Gln
            35                  40                  45

Leu His Phe Ala Tyr Thr Gln Gln Gly Asp Leu Phe Pro Val Ala His
        50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
            100                 105                 110

Phe Thr Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
130                 135                 140

Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His Ile Pro Ala Pro
        210                 215                 220

Arg Pro Glu Glu Phe His Gln Arg Ser Asn Val Thr Leu Thr Leu Arg
225                 230                 235                 240

Asn Leu Lys Arg Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270
```

Pro Glu Met Pro Asp Thr Pro Glu Pro Ile Pro Asp Tyr Met Pro Leu
          275                 280                 285

Trp

<210> SEQ ID NO 27
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 27

Ser Leu Arg Leu Leu Asp His Arg Ala Leu Val Cys Ser Gln Pro Gly
1               5                   10                  15

Leu Ser Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Val Pro Val Ala His
    50                  55                  60

Ile Glu Trp Thr Leu Gln Thr Asp Ala Ser Ile Pro Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
            100                 105                 110

Phe Thr Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp

<210> SEQ ID NO 28
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 28

```
Ser Leu Arg Leu Leu Asp His Arg Ala Leu Val Cys Ser Gln Pro Gly
1               5                   10                  15

Leu Asn Cys Thr Ile Lys Asn Ser Thr Cys Leu Asp Asp Ser Trp Ile
            20                  25                  30

His Pro Arg Asn Leu Thr Pro Ser Pro Lys Asp Leu Gln Ile Gln
        35                  40                  45

Leu His Phe Ala His Thr Gln Gln Gly Asp Leu Val Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His Lys Arg Trp Arg
                100                 105                 110

Phe Thr Phe Ser His Phe Val Val Asp Pro Gly Gln Glu Tyr Glu Val
                115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Pro Arg Met Lys
145                 150                 155                 160

Val Thr Thr Pro Cys Met Ser Gly Ser Leu Trp Asp Pro Asn Ile
                165                 170                 175

Thr Val Glu Thr Leu Glu Ala His Gln Leu Arg Val Ser Phe Thr Leu
                180                 185                 190

Trp Asn Glu Ser Thr His Tyr Gln Ile Leu Leu Thr Ser Phe Pro His
                195                 200                 205

Met Glu Asn His Ser Cys Phe Glu His Met His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro Glu Met Pro Asp Thr Pro Glu Pro Ile Pro Asp Tyr Met Pro Leu
                275                 280                 285

Trp
```

<210> SEQ ID NO 29
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 29

```
Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
            35                  40                  45

Leu His Phe Ala His Thr Gln Gln Gly Asp Leu Phe Pro Val Ala His
    50                  55                  60
```

```
Ile Glu Trp Thr Leu Gln Thr Asp Ala Ser Ile Leu Tyr Leu Glu Gly
 65                  70                  75                  80

Ala Glu Leu Ser Val Leu Gln Leu Ala Thr Asn Glu Arg Leu Cys Val
                 85                  90                  95

Arg Phe Glu Phe Leu Ser Lys Leu Arg His His His Arg Arg Trp Arg
            100                 105                 110

Phe Thr Phe Ser His Phe Val Val Asp Pro Asp Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Ala Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp

<210> SEQ ID NO 30
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 30

Ser Leu Arg Leu Leu Asp His Arg Ala Leu Val Cys Ser Gln Pro Gly
 1               5                  10                  15

Leu Asn Cys Thr Val Lys Asn Ser Thr Cys Leu Asp Asp Ser Trp Ile
                 20                  25                  30

His Pro Arg Asn Leu Thr Pro Ser Ser Pro Lys Asp Leu Gln Ile Gln
            35                  40                  45

Leu His Phe Ala His Thr Gln Gln Gly Asp Leu Phe Pro Val Ala His
        50                  55                  60

Ile Glu Trp Thr Leu Gln Thr Asp Ala Ser Ile Leu Tyr Leu Glu Gly
 65                  70                  75                  80

Ala Glu Leu Ser Val Leu Gln Leu Ala Thr Asn Glu Arg Leu Cys Val
                 85                  90                  95

Arg Phe Glu Phe Leu Ser Lys Leu Arg His His His Arg Arg Trp Arg
            100                 105                 110

Phe Thr Phe Ser His Phe Val Val Asp Pro Asp Gln Glu Tyr Glu Val
        115                 120                 125
```

```
Thr Val His His Leu Pro Lys Pro Ile Pro Asp Gly Asp Pro Asn His
    130                 135                 140
Gln Ser Lys Asn Phe Leu Val Pro Asp Cys Glu His Ala Arg Met Lys
145                 150                 155                 160
Val Thr Thr Pro Cys Met Ser Ser Gly Ser Leu Trp Asp Pro Asn Ile
                165                 170                 175
Thr Val Glu Thr Leu Glu Ala His Gln Leu Arg Val Ser Ile Thr Leu
            180                 185                 190
Trp Asn Glu Ser Thr His Tyr Gln Ile Leu Leu Thr Ser Phe Pro His
                195                 200                 205
Met Glu Asn His Ser Cys Phe Glu His Met His His Ile Pro Ala Pro
    210                 215                 220
Arg Pro Glu Glu Phe His Gln Arg Ser Asn Val Thr Leu Thr Leu Arg
225                 230                 235                 240
Asn Leu Lys Gly Cys Cys Arg His Gln Val Gln Ile Gln Pro Phe Phe
                245                 250                 255
Ser Ser Cys Leu Asn Asp Cys Leu Arg His Ser Ala Thr Val Ser Cys
            260                 265                 270
Pro Glu Met Pro Asp Thr Pro Glu Pro Ile Pro Asp Tyr Met Pro Leu
                275                 280                 285
Trp

<210> SEQ ID NO 31
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 31

Ser Leu Arg Leu Leu Asp His Arg Ala Leu Val Cys Ser Gln Pro Gly
1               5                   10                  15
Leu Asn Cys Thr Val Lys Asn Ser Thr Cys Leu Asp Asp Ser Trp Ile
                20                  25                  30
His Pro Arg Asn Leu Thr Pro Ser Ser Pro Lys Asp Leu Gln Ile Gln
            35                  40                  45
Leu His Phe Ala His Thr Gln Gln Gly Asp Leu Val Pro Val Ala His
    50                  55                  60
Ile Glu Trp Thr Leu Gln Thr Asp Ala Ser Ile Leu Tyr Leu Glu Gly
65                  70                  75                  80
Ala Glu Leu Ser Val Leu Gln Leu Asn Thr Asn Glu Arg Leu Cys Val
                85                  90                  95
Arg Phe Glu Phe Leu Ser Lys Leu Arg His His His Lys Arg Trp Arg
            100                 105                 110
Phe Thr Phe Ser His Phe Val Val Asp Pro Gly Gln Glu Tyr Glu Val
        115                 120                 125
Thr Val Tyr His Leu Pro Lys Pro Ile Pro Asp Gly Asp Pro Asn His
    130                 135                 140
Gln Ser Lys Asn Phe Leu Val Pro Asp Cys Glu His Pro Arg Met Lys
145                 150                 155                 160
Val Thr Thr Pro Cys Met Ser Ser Gly Ser Leu Trp Asp Pro Asn Ile
                165                 170                 175
Thr Val Glu Thr Leu Glu Ala His Gln Leu Arg Val Ser Phe Thr Leu
            180                 185                 190
Trp Asn Glu Ser Thr His Tyr Gln Ile Leu Leu Thr Ser Phe Pro His
```

```
                   195                 200                 205
Arg Glu Asn His Ser Cys Phe Glu His Met His His Ile Pro Ala Pro
    210                 215                 220
Arg Pro Glu Glu Phe His Gln Arg Ser Asn Val Thr Leu Thr Leu Arg
225                 230                 235                 240
Asn Leu Lys Gly Cys Cys Arg His Gln Val Gln Ile Gln Pro Phe Phe
                245                 250                 255
Ser Ser Cys Leu Asn Asp Cys Leu Arg His Ser Ala Thr Val Ser Cys
            260                 265                 270
Pro Glu Met Pro Asp Thr Pro Glu Pro Ile Pro Asp Tyr Met Pro Leu
        275                 280                 285
Trp

<210> SEQ ID NO 32
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 32

Ser Leu Arg Leu Leu Asp His Arg Ala Leu Val Cys Ser Gln Pro Gly
1               5                   10                  15
Leu Asn Cys Thr Val Lys Asn Ser Thr Cys Leu Asp Asp Ser Trp Ile
                20                  25                  30
His Pro Arg Asn Leu Thr Pro Ser Ser Pro Lys Asp Leu Gln Ile Gln
            35                  40                  45
Leu His Phe Ala Tyr Thr Gln Gln Gly Asp Leu Val Pro Val Ala His
        50                  55                  60
Ile Glu Trp Thr Leu Gln Thr Asp Ala Ser Ile Leu Tyr Leu Glu Gly
65                  70                  75                  80
Ala Glu Leu Ser Val Leu Gln Leu Asn Thr Asn Glu Arg Leu Cys Val
                85                  90                  95
Arg Phe Glu Phe Leu Ser Lys Leu Arg His His His Lys Arg Trp Arg
                100                 105                 110
Phe Thr Phe Ser His Phe Val Val Asp Pro Gly Gln Glu Tyr Glu Val
            115                 120                 125
Thr Val His His Leu Pro Lys Pro Ile Pro Asp Gly Asp Pro Asn His
        130                 135                 140
Gln Ser Lys Asn Phe Leu Val Pro Asp Cys Glu His Pro Arg Met Lys
145                 150                 155                 160
Val Thr Thr Pro Cys Met Ser Ser Gly Ser Leu Trp Asp Pro Asn Ile
                165                 170                 175
Thr Val Glu Thr Leu Glu Ala His Gln Leu Arg Val Ser Phe Thr Leu
                180                 185                 190
Trp Asn Glu Ser Thr His Tyr Gln Ile Leu Leu Thr Ser Phe Pro His
            195                 200                 205
Met Glu Asn His Ser Cys Phe Glu His Met His His Ile Pro Ala Pro
        210                 215                 220
Arg Pro Glu Glu Phe His Gln Arg Ser Asn Val Thr Leu Thr Leu Arg
225                 230                 235                 240
Asn Leu Lys Gly Cys Cys Arg His Gln Val Gln Ile Gln Pro Phe Phe
                245                 250                 255
Ser Ser Cys Leu Asn Asp Cys Leu Arg His Ser Ala Thr Val Ser Cys
            260                 265                 270
```

```
Pro Glu Met Pro Asp Thr Pro Glu Pro Ile Pro Asp Tyr Met Pro Leu
            275                 280                 285

Trp

<210> SEQ ID NO 33
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 33

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Val Pro Val Ala His
    50                  55                  60

Ile Glu Trp Thr Leu Gln Thr Asp Ala Ser Ile Leu Tyr Leu Lys Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Lys Arg Trp Arg
            100                 105                 110

Phe Thr Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
        195                 200                 205

Met Glu Asn His Ser Cys Phe Glu His Met His His Ile Pro Ala Pro
    210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
        275                 280                 285

Trp

<210> SEQ ID NO 34
<211> LENGTH: 289
<212> TYPE: PRT
<213> ORGANISM: Artificial Sequence
<220> FEATURE:
<223> OTHER INFORMATION: Artificial Variant of IL17RA-ECD
```

<400> SEQUENCE: 34

```
Ser Leu Arg Leu Leu Asp His Arg Ala Leu Val Cys Ser Gln Pro Gly
1               5                   10                  15

Leu Ser Cys Thr Val Lys Asn Ser Thr Cys Leu Asp Asp Ser Trp Ile
            20                  25                  30

His Pro Arg Asn Leu Thr Pro Ser Ser Pro Lys Asp Leu Gln Ile Gln
        35                  40                  45

Leu His Phe Ala His Thr Gln Gln Gly Asp Leu Val Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Ala Thr Asn Glu Arg Leu Cys Val
                85                  90                  95

Arg Phe Glu Phe Leu Ser Lys Leu Arg His His Lys Arg Trp Arg
            100                 105                 110

Phe Thr Phe Ser His Phe Val Val Asp Pro Gly Gln Glu Tyr Glu Val
            115                 120                 125

Thr Val His His Leu Pro Lys Pro Ile Pro Asp Gly Asp Pro Asn His
        130                 135                 140

Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
            195                 200                 205

Met Glu Asn His Ser Cys Phe Glu His Met His His Ile Pro Ala Pro
        210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
            260                 265                 270

Pro Glu Met Pro Asp Thr Pro Glu Pro Ile Pro Asp Tyr Met Pro Leu
            275                 280                 285

Trp
```

<210> SEQ ID NO 35
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 35

```
Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
            20                  25                  30

Tyr Pro Arg Asn Leu Thr Pro Ser Ser Pro Lys Asp Leu Gln Ile Gln
        35                  40                  45

Leu His Phe Ala His Thr Gln Gln Gly Asp Leu Val Pro Val Ala His
```

```
                50                  55                  60
Ile Glu Trp Thr Leu Gln Thr Asp Ala Ser Ile Leu Tyr Leu Glu Gly
 65                  70                  75                  80

Ala Glu Leu Ser Val Leu Gln Leu Asn Thr Asn Glu Arg Leu Cys Val
                 85                  90                  95

Arg Phe Glu Phe Leu Ser Lys Leu Arg His His Lys Arg Trp Arg
                100                 105                 110

Phe Thr Phe Ser His Phe Val Val Asp Pro Gly Gln Glu Tyr Glu Val
                115                 120                 125

Thr Val His His Leu Pro Lys Pro Ile Pro Asp Gly Asp Pro Asn His
                130                 135                 140

Gln Ser Lys Asn Phe Leu Val Pro Asp Cys Glu His Pro Arg Met Lys
145                 150                 155                 160

Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
                180                 185                 190

Trp Asn Glu Ser Thr His Tyr Gln Val Leu Leu Thr Ser Phe Pro His
                195                 200                 205

Met Glu Asn His Ser Cys Phe Glu His Met His His Ile Pro Ala Pro
                210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro Glu Met Pro Asp Thr Pro Glu Pro Ile Pro Asp Tyr Met Pro Leu
                275                 280                 285

Trp

<210> SEQ ID NO 36
<211> LENGTH: 289
<212> TYPE: PRT
<213> ORGANISM: Artificial Sequence
<220> FEATURE:
<223> OTHER INFORMATION: Artificial Variant of IL17RA-ECD

<400> SEQUENCE: 36

Ser Leu Arg Leu Leu Asp His Arg Ala Leu Val Cys Ser Gln Pro Gly
 1               5                  10                  15

Leu Asn Cys Thr Val Lys Asn Ser Thr Cys Leu Asp Asp Ser Trp Ile
                20                  25                  30

His Pro Arg Asn Leu Thr Pro Ser Ser Pro Lys Asp Leu Gln Ile Gln
                35                  40                  45

Leu His Phe Ala His Thr Gln Gln Gly Asp Leu Val Pro Val Ala His
                50                  55                  60

Ile Glu Trp Thr Leu Gln Thr Asp Ala Ser Ile Leu Tyr Leu Lys Gly
 65                  70                  75                  80

Ala Glu Leu Ser Val Leu Gln Leu Asn Thr Asn Glu Arg Leu Cys Val
                 85                  90                  95

Arg Phe Glu Phe Leu Ser Lys Leu Arg His His His Lys Arg Trp Arg
                100                 105                 110

Leu Thr Phe Ser His Phe Val Val Asp Pro Gly Gln Glu Tyr Glu Val
                115                 120                 125
```

```
Thr Val His His Leu Pro Lys Pro Ile Pro Asp Gly Asp Pro Asn His
    130                 135                 140
Gln Ser Lys Asn Phe Leu Val Pro Asp Cys Glu His Pro Arg Met Lys
145                 150                 155                 160
Val Thr Thr Pro Cys Met Ser Ser Gly Ser Leu Trp Asp Pro Asn Ile
                165                 170                 175
Thr Val Glu Thr Leu Glu Ala His Gln Leu Arg Val Ser Phe Thr Leu
            180                 185                 190
Trp Asn Glu Ser Thr His Tyr Gln Ile Leu Leu Thr Ser Phe Pro His
        195                 200                 205
Met Glu Asn His Ser Cys Phe Glu His Met His Ile Pro Ala Pro
210                 215                 220
Arg Pro Glu Glu Phe His Gln Arg Ser Asn Val Thr Leu Thr Leu Arg
225                 230                 235                 240
Asn Leu Lys Gly Cys Cys Arg His Gln Val Gln Ile Gln Pro Phe Phe
                245                 250                 255
Ser Ser Cys Leu Asn Asp Cys Leu Arg His Ser Ala Thr Val Ser Cys
            260                 265                 270
Pro Glu Met Pro Asp Thr Pro Glu Pro Ile Pro Asp Tyr Met Pro Leu
        275                 280                 285
Trp

<210> SEQ ID NO 37
<211> LENGTH: 289
<212> TYPE: PRT
<213> ORGANISM: Artificial Sequence
<220> FEATURE:
<223> OTHER INFORMATION: Artificial Variant of IL17RA-ECD
<220> FEATURE:
<221> NAME/KEY: MISC_FEATURE
<222> LOCATION: (10)..(10)
<223> OTHER INFORMATION: Xaa is leucine or proline
<220> FEATURE:
<221> NAME/KEY: MISC_FEATURE
<222> LOCATION: (15)..(15)
<223> OTHER INFORMATION: Xaa is proline or glutamic acid
<220> FEATURE:
<221> NAME/KEY: MISC_FEATURE
<222> LOCATION: (44)..(44)
<223> OTHER INFORMATION: Xaa is aspartic acid or aspargine
<220> FEATURE:
<221> NAME/KEY: MISC_FEATURE
<222> LOCATION: (45)..(45)
<223> OTHER INFORMATION: Xaa is leucine, valine or isoleucine
<220> FEATURE:
<221> NAME/KEY: MISC_FEATURE
<222> LOCATION: (56)..(56)
<223> OTHER INFORMATION: Xaa is glutamine or histidine
<220> FEATURE:
<221> NAME/KEY: MISC_FEATURE
<222> LOCATION: (60)..(60)
<223> OTHER INFORMATION: Xaa is phenylalanine, leucine, or valine
<220> FEATURE:
<221> NAME/KEY: MISC_FEATURE
<222> LOCATION: (97)..(97)
<223> OTHER INFORMATION: Xaa is arginine or lysine
<220> FEATURE:
<221> NAME/KEY: MISC_FEATURE
<222> LOCATION: (109)..(109)
<223> OTHER INFORMATION: Xaa is arginine or lysine
<220> FEATURE:
<221> NAME/KEY: MISC_FEATURE
<222> LOCATION: (123)..(123)
<223> OTHER INFORMATION: Xaa is aspartic acid or glycine
<220> FEATURE:
<221> NAME/KEY: MISC_FEATURE
<222> LOCATION: (156)..(156)
```

```
<223> OTHER INFORMATION: Xaa is histidine or aspartic acid
<220> FEATURE:
<221> NAME/KEY: MISC_FEATURE
<222> LOCATION: (157)..(157)
<223> OTHER INFORMATION: Xaa is alanine or proline
<220> FEATURE:
<221> NAME/KEY: MISC_FEATURE
<222> LOCATION: (240)..(240)
<223> OTHER INFORMATION: Xaa is arginine or serine
<220> FEATURE:
<221> NAME/KEY: MISC_FEATURE
<222> LOCATION: (244)..(244)
<223> OTHER INFORMATION: Xaa is glycine, tryptophan or arginine
<220> FEATURE:
<221> NAME/KEY: MISC_FEATURE
<222> LOCATION: (249)..(249)
<223> OTHER INFORMATION: Xaa is glutamine or histidine
<220> FEATURE:
<221> NAME/KEY: MISC_FEATURE
<222> LOCATION: (268)..(268)
<223> OTHER INFORMATION: Xaa is alanine or valine
<220> FEATURE:
<221> NAME/KEY: MISC_FEATURE
<222> LOCATION: (271)..(271)
<223> OTHER INFORMATION: Xaa is serine or proline

<400> SEQUENCE: 37

Ser Leu Arg Leu Leu Asp His Arg Ala Xaa Val Cys Ser Gln Xaa Gly
1               5                   10                  15

Leu Asn Cys Thr Val Lys Asn Ser Thr Cys Leu Asp Asp Ser Trp Ile
            20                  25                  30

His Pro Arg Asn Leu Thr Pro Ser Pro Lys Xaa Xaa Gln Ile Gln
        35                  40                  45

Leu His Phe Ala His Thr Gln Xaa Gly Asp Leu Xaa Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Xaa Phe Glu Phe Leu Ser Lys Leu Arg His His His Xaa Arg Trp Arg
            100                 105                 110

Phe Thr Phe Ser His Phe Val Val Asp Pro Xaa Gln Glu Tyr Glu Val
            115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu Xaa Xaa Arg Met Lys
145                 150                 155                 160

Val Thr Thr Pro Cys Met Ser Ser Gly Ser Leu Trp Asp Pro Asn Ile
            165                 170                 175

Thr Val Glu Thr Leu Glu Ala His Gln Leu Arg Val Ser Phe Thr Leu
            180                 185                 190

Trp Asn Glu Ser Thr His Tyr Gln Ile Leu Leu Thr Ser Phe Pro His
            195                 200                 205

Met Glu Asn His Ser Cys Phe Glu His Met His His Ile Pro Ala Pro
210                 215                 220

Arg Pro Glu Glu Phe His Gln Arg Ser Asn Val Thr Leu Thr Leu Xaa
225                 230                 235                 240

Asn Leu Lys Xaa Cys Cys Arg His Xaa Val Gln Ile Gln Pro Phe Phe
            245                 250                 255

Ser Ser Cys Leu Asn Asp Cys Leu Arg His Ser Xaa Thr Val Xaa Cys
            260                 265                 270
```

```
Pro Glu Met Pro Asp Thr Pro Glu Pro Ile Pro Asp Tyr Met Pro Leu
        275                 280                 285
Trp

<210> SEQ ID NO 38
<211> LENGTH: 18
<212> TYPE: DNA
<213> ORGANISM: Artificial Sequence
<220> FEATURE:
<223> OTHER INFORMATION: ECD-nested-Not primer for hIL17RA-ECD

<400> SEQUENCE: 38
gtggtggtgg tggtgctc                                                   18

<210> SEQ ID NO 39
<211> LENGTH: 20
<212> TYPE: DNA
<213> ORGANISM: Artificial Sequence
<220> FEATURE:
<223> OTHER INFORMATION: ECD-nested-Nco, primer for hIL17RA-ECD

<400> SEQUENCE: 39
gtaccgacga cgacgacaag                                                 20

<210> SEQ ID NO 40
<211> LENGTH: 34
<212> TYPE: DNA
<213> ORGANISM: Artificial Sequence
<220> FEATURE:
<223> OTHER INFORMATION: fr-pCTCON-ECD IL17RA, primer for hIL17RA-ECD

<400> SEQUENCE: 40
ataaacgcta gctccctgcg actcctggac cacc                                 34

<210> SEQ ID NO 41
<211> LENGTH: 39
<212> TYPE: DNA
<213> ORGANISM: Artificial Sequence
<220> FEATURE:
<223> OTHER INFORMATION: rev-pCTCON-ECD IL17RA, primer for hIL17RA-ECD

<400> SEQUENCE: 41
tagatgtcgg atccgtacac ccacaggggc atgtagtcc                            39

<210> SEQ ID NO 42
<211> LENGTH: 70
<212> TYPE: DNA
<213> ORGANISM: Artificial Sequence
<220> FEATURE:
<223> OTHER INFORMATION: fr-pCTCON-ECD hr, primer for hIL17RA-ECD

<400> SEQUENCE: 42
ggtggtggtt ctggtggtgg tggttctggt ggtggtggtt ctgctagctc cctgcgactc     60
ctggaccacc                                                            70

<210> SEQ ID NO 43
<211> LENGTH: 76
<212> TYPE: DNA
<213> ORGANISM: Artificial Sequence
<220> FEATURE:
<223> OTHER INFORMATION: rev-pCTCON-ECD hr, primer for hIL17RA-ECD,
      primer for hIL17RA-ECD

<400> SEQUENCE: 43
gatctcgagc tattacaagt cctcttcaga aataagcttt tgttcggatc cgtacaccca     60
``` cagggggcatg tagtcc                                                        76

<210> SEQ ID NO 44
<211> LENGTH: 22
<212> TYPE: DNA
<213> ORGANISM: Artificial Sequence
<220> FEATURE:
<223> OTHER INFORMATION: fr- ECD, primer for hIL17RA-ECD

<400> SEQUENCE: 44
tccctgcgac tcctggacca cc                                                  22

<210> SEQ ID NO 45
<211> LENGTH: 25
<212> TYPE: DNA
<213> ORGANISM: Artificial Sequence
<220> FEATURE:
<223> OTHER INFORMATION: rev-ECD, primer for hIL17RA-ECD

<400> SEQUENCE: 45
gtacacccac aggggcatgt agtcc                                               25

<210> SEQ ID NO 46
<211> LENGTH: 38
<212> TYPE: DNA
<213> ORGANISM: Artificial Sequence
<220> FEATURE:
<223> OTHER INFORMATION: fr-pET32-ECD/Nco, primer for hIL17RA-ECD

<400> SEQUENCE: 46
attcgatgcc atggcctccc tgcgactcct ggaccacc                                 38

<210> SEQ ID NO 47
<211> LENGTH: 49
<212> TYPE: DNA
<213> ORGANISM: Artificial Sequence
<220> FEATURE:
<223> OTHER INFORMATION: rev-pET32-ECD/Not, primer for hIL17RA-ECD

<400> SEQUENCE: 47
tcactcagtg cggccgccta ttagtacacc cacagggggca tgtagtccg                    49

<210> SEQ ID NO 48
<211> LENGTH: 35
<212> TYPE: DNA
<213> ORGANISM: Artificial Sequence
<220> FEATURE:
<223> OTHER INFORMATION: fr-ECD-Nco-pFC, primer for hIL17RA-ECD

<400> SEQUENCE: 48
ccatggttct gcgactcctg gaccaccggg cgctg                                    35

<210> SEQ ID NO 49
<211> LENGTH: 26
<212> TYPE: DNA
<213> ORGANISM: Artificial Sequence
<220> FEATURE:
<223> OTHER INFORMATION: rev-ECD-Xba-pFC, primer for hIL17RA-ECD

<400> SEQUENCE: 49
tctagaccac aggggcatgt agtccg                                              26

<210> SEQ ID NO 50
<211> LENGTH: 30
<212> TYPE: DNA

```
<213> ORGANISM: Artificial Sequence
<220> FEATURE:
<223> OTHER INFORMATION: fr-ECD-Bam-pFC, primer for hIL17RA-ECD

<400> SEQUENCE: 50
ggatcctaga gaggcttgtg gggcctcagg                                    30

<210> SEQ ID NO 51
<211> LENGTH: 29
<212> TYPE: DNA
<213> ORGANISM: Artificial Sequence
<220> FEATURE:
<223> OTHER INFORMATION: rev-ECD-SalI-pFC, primer for hIL17RA-ECD

<400> SEQUENCE: 51
gtcgacgccc acagggggcat gtagtccgg                                    29

<210> SEQ ID NO 52
<211> LENGTH: 31
<212> TYPE: DNA
<213> ORGANISM: Artificial Sequence
<220> FEATURE:
<223> OTHER INFORMATION: L10P, primer for hIL17RA-ECD mutant library

<400> SEQUENCE: 52
tggaccaccg ggcgccggtc tgctcccagc c                                  31

<210> SEQ ID NO 53
<211> LENGTH: 33
<212> TYPE: DNA
<213> ORGANISM: Artificial Sequence
<220> FEATURE:
<223> OTHER INFORMATION: P15E, primer for hIL17RA-ECD mutant library

<400> SEQUENCE: 53
ctggtctgct cccaggaagg gctaaactgc acg                                33

<210> SEQ ID NO 54
<211> LENGTH: 30
<212> TYPE: DNA
<213> ORGANISM: Artificial Sequence
<220> FEATURE:
<223> OTHER INFORMATION: D44N, primer for hIL17RA-ECD mutant library

<400> SEQUENCE: 54
cctcctcccc aaagaacctg cagatccagc                                    30

<210> SEQ ID NO 55
<211> LENGTH: 33
<212> TYPE: DNA
<213> ORGANISM: Artificial Sequence
<220> FEATURE:
<223> OTHER INFORMATION: L45I, primer for hIL17RA-ECD mutant library

<400> SEQUENCE: 55
tcctccccaa aggacattca gatccagctg cac                                33

<210> SEQ ID NO 56
<211> LENGTH: 32
<212> TYPE: DNA
<213> ORGANISM: Artificial Sequence
<220> FEATURE:
<223> OTHER INFORMATION: L45V, primer for hIL17RA-ECD mutant library

<400> SEQUENCE: 56
ctcctcccca aggacgtgc agatccagct gc                                  32
```

<210> SEQ ID NO 57
<211> LENGTH: 28
<212> TYPE: DNA
<213> ORGANISM: Artificial Sequence
<220> FEATURE:
<223> OTHER INFORMATION: Q56H, primer for hIL17RA-ECD mutant library

<400> SEQUENCE: 57
cccacaccca acatggagac ctgttccc                                28

<210> SEQ ID NO 58
<211> LENGTH: 33
<212> TYPE: DNA
<213> ORGANISM: Artificial Sequence
<220> FEATURE:
<223> OTHER INFORMATION: F60V, primer for hIL17RA-ECD mutant library

<400> SEQUENCE: 58
caacaaggag acctggtgcc cgtggctcac atc                          33

<210> SEQ ID NO 59
<211> LENGTH: 33
<212> TYPE: DNA
<213> ORGANISM: Artificial Sequence
<220> FEATURE:
<223> OTHER INFORMATION: F60L, primer for hIL17RA-ECD mutant library

<400> SEQUENCE: 59
caacaaggag acctgctgcc cgtggctcac atc                          33

<210> SEQ ID NO 60
<211> LENGTH: 30
<212> TYPE: DNA
<213> ORGANISM: Artificial Sequence
<220> FEATURE:
<223> OTHER INFORMATION: R97K, primer for hIL17RA-ECD mutant library

<400> SEQUENCE: 60
cgtttgtgcg tcaaatttga gtttctgtcc                              30

<210> SEQ ID NO 61
<211> LENGTH: 32
<212> TYPE: DNA
<213> ORGANISM: Artificial Sequence
<220> FEATURE:
<223> OTHER INFORMATION: R109K, primer

<400> SEQUENCE: 61
tgaggcatca ccacaaacgg tggcgtttta cc                           32

<210> SEQ ID NO 62
<211> LENGTH: 30
<212> TYPE: DNA
<213> ORGANISM: Artificial Sequence
<220> FEATURE:
<223> OTHER INFORMATION: D123G, primer

<400> SEQUENCE: 62
gtggttgacc ctggccagga atatgaggtg                              30

<210> SEQ ID NO 63
<211> LENGTH: 31
<212> TYPE: DNA
<213> ORGANISM: Artificial Sequence
<220> FEATURE:

```
<223> OTHER INFORMATION: H156D, primer

<400> SEQUENCE: 63
gtgcctgact gtgaggatgc caggatgaag g                                    31

<210> SEQ ID NO 64
<211> LENGTH: 32
<212> TYPE: DNA
<213> ORGANISM: Artificial Sequence
<220> FEATURE:
<223> OTHER INFORMATION: A157P, primer

<400> SEQUENCE: 64
ctgactgtga gcatccgagg atgaaggtaa cc                                   32

<210> SEQ ID NO 65
<211> LENGTH: 30
<212> TYPE: DNA
<213> ORGANISM: Artificial Sequence
<220> FEATURE:
<223> OTHER INFORMATION: R240S, primer

<400> SEQUENCE: 65
cacactcact ctaagcaacc ttaaagggtg                                      30

<210> SEQ ID NO 66
<211> LENGTH: 29
<212> TYPE: DNA
<213> ORGANISM: Artificial Sequence
<220> FEATURE:
<223> OTHER INFORMATION: G244W, primer

<400> SEQUENCE: 66
acgcaacctt aaatggtgct gtcgccacc                                       29

<210> SEQ ID NO 67
<211> LENGTH: 29
<212> TYPE: DNA
<213> ORGANISM: Artificial Sequence
<220> FEATURE:
<223> OTHER INFORMATION: Q249H, primer

<400> SEQUENCE: 67
gtgctgtcgc caccatgtgc agatccagc                                       29

<210> SEQ ID NO 68
<211> LENGTH: 31
<212> TYPE: DNA
<213> ORGANISM: Artificial Sequence
<220> FEATURE:
<223> OTHER INFORMATION: A268V, primer

<400> SEQUENCE: 68
gcctcagaca ctccgtgact gtttcctgcc c                                    31

<210> SEQ ID NO 69
<211> LENGTH: 32
<212> TYPE: DNA
<213> ORGANISM: Artificial Sequence
<220> FEATURE:
<223> OTHER INFORMATION: S271P, primer

<400> SEQUENCE: 69
cactccgcga ctgttccgtg cccagaaatg cc                                   32
```

-continued

```
<210> SEQ ID NO 70
<211> LENGTH: 21
<212> TYPE: DNA
<213> ORGANISM: Artificial Sequence
<220> FEATURE:
<223> OTHER INFORMATION: fr-pET32-seq, primer

<400> SEQUENCE: 70
ttcctcgacg ctaacctggc c                                              21

<210> SEQ ID NO 71
<211> LENGTH: 22
<212> TYPE: DNA
<213> ORGANISM: Artificial Sequence
<220> FEATURE:
<223> OTHER INFORMATION: rev-pET32-seq, primer

<400> SEQUENCE: 71
agcagccgga tctcagtggt gg                                             22

<210> SEQ ID NO 72
<211> LENGTH: 33
<212> TYPE: DNA
<213> ORGANISM: Artificial Sequence
<220> FEATURE:
<223> OTHER INFORMATION: fr-pCTCON-lib, primer

<400> SEQUENCE: 72
gacgattgaa ggtagatacc catacgacgt tcc                                 33

<210> SEQ ID NO 73
<211> LENGTH: 31
<212> TYPE: DNA
<213> ORGANISM: Artificial Sequence
<220> FEATURE:
<223> OTHER INFORMATION: rev-pCTCON-lib, primer

<400> SEQUENCE: 73
cagatctcga gctattacaa gtcctcttca g                                   31

<210> SEQ ID NO 74
<211> LENGTH: 22
<212> TYPE: DNA
<213> ORGANISM: Artificial Sequence
<220> FEATURE:
<223> OTHER INFORMATION: pFC-fr, primer

<400> SEQUENCE: 74
gttttctgtt ctgcgccgtt ac                                             22

<210> SEQ ID NO 75
<211> LENGTH: 66
<212> TYPE: PRT
<213> ORGANISM: Artificial Sequence
<220> FEATURE:
<223> OTHER INFORMATION: pFC-rev, primer

<400> SEQUENCE: 75

Gly Leu Tyr Cys Tyr Ser Ala Leu Ala Thr His Arg Thr His Arg Cys
1               5                   10                  15

Tyr Ser Thr His Arg Ala Leu Ala Gly Leu Tyr Thr His Arg Thr His
            20                  25                  30

Arg Gly Leu Tyr Thr His Arg Gly Leu Tyr Gly Leu Tyr Thr His Arg
        35                  40                  45
```

```
Thr His Arg Thr His Arg Gly Leu Tyr Thr His Arg Cys Tyr Ser Cys
    50                  55                  60

Tyr Ser
65

<210> SEQ ID NO 76
<211> LENGTH: 24
<212> TYPE: DNA
<213> ORGANISM: Artificial Sequence
<220> FEATURE:
<223> OTHER INFORMATION: pFC-rev-in, primer

<400> SEQUENCE: 76
catgagggtg tccttgggtt ttgg                                          24
```

IL-17R-ECD MUTANTS AND METHODS OF USING SAME

This application is a continuation of U.S. patent application Ser. No. 14/232,921, filed on Aug. 18, 2014 (now U.S. Pat. No. 9,416,168); which claims priority as a 371 of international application number PCT/IB2012/001400, filed on Jul. 18, 2012; which claims priority to U.S. provisional patent application Ser. No. 61/509,236, filed on Jul. 19, 2011.

FIELD

The presently described subject matter relates to mutant IL17RA-ECD peptides, and to their use in the treatment and/or prevention of inflammatory disorders.

BACKGROUND

Interleukin 17 (IL-17) is a family of proinflammatory cytokines consisting of six members (IL17A-F). hIL-17A is expressed by a unique lineage of CD4 T cells (Th-17) and is known to stimulate fibroblasts, endothelial, epithelial cells and macrophages to produce multiple proinflammatory mediators. These mediators include IL-1, IL-6, TNF-α, NOS-2 and chemokines, resulting in the induction of inflammation (Aggarwal, S. Journal of Biological Chemistry 278, 1910-1914 (2003)). Evidence from animal studies indicates that hIL-17A and hIL-17F are crucial for coordinating local host defense against certain bacteria and fungi in mammals. Recent studies also show that hIL-17 is actively involved in a range of pathologic conditions in humans, ranging from common asthma to several autoimmune diseases, such as rheumatoid arthritis, psoriasis and inflammatory bowel disease, as well as allergen-specific immune responses (Kolls, J. K. Immunity 21, 467-476 (2004); Iwakura, Y. The Journal of Clinical Investigation 116, 1218-1222 (2006); Nakae, S. et al. Immunity 17, 375-387 (2002)). The signaling of hIL-17 in several cell types is mediated by binding to endogenous hIL-17 receptors (hIL-17R) that contain five receptor types, IL-17RA-IL-17RE (Aggarwal, S. Journal of Leukocyte Biology 71, 1-8 (2002)). Recently it was shown that hIL-17A signaling is mediated by a heteromeric complex containing, hIL-17RA and hIL-17RC chains (Toy, D. et al. The Journal of Immunology 177, 36-39 (2006)). Both receptors are single transmembrane proteins of ~90 kDa, and contain conserved structural motifs (Kramer, J. M. et al. The Journal of Immunology 179, 6379-6383 (2007); Gaffen, S. L. Nat Rev Immunol 9, 556-567 (2009)). The IL-17R receptors are not homologues to any known receptors and possess unique signaling properties, which enable Th-17 cells to act as a bridge between cells of the innate and adaptive immune systems (Ely, L. K., Nat Immunol 10, 1245-1251 (2009)).

A crystal structure of hIL-17RA extra cellular domain (ECD) bound to hIL-17F has been recently published, revealing new insight into the molecular basis for IL-17 ligand and receptor interactions (Ely, L. K., Nat Immunol 10, 1245-1251 (2009)). Three main interaction sites at the binding interface were detected, Thr25-Trp31 (site 1), Leu86-Arg93 (site 2) and Cys259-Arg265 (site 3), site 2 being the most prominent interface of the complex (Ely, L. K., Nat Immunol 10, 1245-1251 (2009)). The structure showed one hIL-17RA bound to the dimeric hIL-17F cytokine, leaving the second potential receptor-binding interface free to engage to a second receptor.

SUMMARY

The present inventors have engineered soluble IL17 receptors for enhanced affinity, thermostability, and biological activity relative to the wild-type receptor. Thus, the presently described engineered soluble hIL-17RA receptors are useful for treating and/or preventing inflammation as well as various inflammatory disorders that, for example, involve hIL-17 activity.

Engineered soluble hIL-17RA receptors with high affinity to hIL-17 that inhibit downstream IL17A induced signaling events in cells have been developed. A mutant library of hIL17RA extracellular domain was generated, expressed and screened for mutants with increased binding affinity to hIL17A relative to the WT IL17RA soluble receptor. Selected variants showing increased expression in E. coli cells were further expressed in mammalian cells, purified and examined. Two hIL17RA-ECD variants, V3 and V10, were found to be more thermostable and bind hIL-17A with up to 6-fold higher affinity relative to the WT hIL17RA-ECD. The V3 and V10 variants contain six and five mutations, respectively which are mainly found on the protein surface distal from the active site. These variants were further examined using a cell based assay for inhibition of hIL-17A induced secretion of CXCL1 and IL-6 by human fibroblasts. Both V3 and V10 inhibited hIL-17A induced IL-6 and CXCL1 secretion by human fibroblasts at lower concentrations than the WT hIL17RA-ECD. These newly discovered IL17RA mutants are useful therapeutic agents for the treatment of disorders that involve hIL-17A activity, including for example, inflammation and/or inflammatory disorders.

The presently described subject matter is directed to an IL17RA-ECD mutant comprising or consisting of the amino acid sequence of SEQ ID NO: 37.

The presently described subject matter further provides an IL17RA-ECD mutant comprising or consisting of the amino acid sequence of SEQ ID NO: 37, wherein position 10 of SEQ ID NO: 37 is proline.

In addition, the presently described subject matter provides an IL17RA-ECD mutant comprising or consisting of the amino acid sequence of SEQ ID NO: 37, wherein position 15 of SEQ ID NO: 37 is glutamic acid.

Further, the presently described subject matter provides an IL17RA-ECD mutant comprising or consisting of the amino acid sequence of SEQ ID NO: 37, wherein position 44 of SEQ ID NO: 37 is asparagine.

The presently described subject matter provides an IL17RA-ECD mutant comprising or consisting of the amino acid sequence of SEQ ID NO: 37, wherein position 45 of SEQ ID NO: 37 is valine or isoleucine.

The presently described subject matter also provides an IL17RA-ECD mutant comprising or consisting of the amino acid sequence of SEQ ID NO: 37, wherein position 56 of SEQ ID NO: 37 is histidine.

The presently described subject matter provides an IL17RA-ECD mutant comprising or consisting of the amino acid sequence of SEQ ID NO: 37, wherein position 60 of SEQ ID NO: 37 is leucine or valine.

Yet further, the presently described subject matter provides an IL17RA-ECD mutant comprising or consisting of the amino acid sequence of SEQ ID NO: 37, wherein position 97 of SEQ ID NO: 37 is lysine.

The presently described subject matter provides an IL17RA-ECD mutant comprising or consisting of the amino acid sequence of SEQ ID NO: 37, wherein position 109 of SEQ ID NO: 37 is lysine.

The presently described subject matter further provides an IL17RA-ECD mutant comprising or consisting of the amino acid sequence of SEQ ID NO: 37, wherein position 123 of SEQ ID NO: 37 is glycine.

The presently described subject matter yet further provides an IL17RA-ECD mutant comprising or consisting of the amino acid sequence of SEQ ID NO: 37, wherein position 156 of SEQ ID NO: 37 is aspartic acid.

The presently described subject matter provides an IL17RA-ECD mutant comprising or consisting of the amino acid sequence of SEQ ID NO: 37, wherein position 157 of SEQ ID NO: 37 is proline.

The presently described subject matter provides an IL17RA-ECD mutant comprising or consisting of the amino acid sequence of SEQ ID NO: 37, wherein position 240 of SEQ ID NO: 37 is serine.

The presently described subject matter also provides an IL17RA-ECD mutant comprising or consisting of the amino acid sequence of SEQ ID NO: 37, wherein position 244 of SEQ ID NO: 37 is tryptophan or arginine.

The presently described subject further matter provides an IL17RA-ECD mutant comprising or consisting of the amino acid sequence of SEQ ID NO: 37, wherein position 249 of SEQ ID NO: 37 is histidine.

Yet further, the presently described subject matter provides an IL17RA-ECD mutant comprising or consisting of the amino acid sequence of SEQ ID NO: 37, wherein position 268 of SEQ ID NO: 37 is valine.

The presently described subject matter also provides an IL17RA-ECD mutant comprising or consisting of the amino acid sequence of SEQ ID NO: 37, wherein position 271 of SEQ ID NO: 37 is proline.

The presently described subject matter further provides an IL17RA-ECD mutant comprising or consisting of the amino acid sequence of SEQ ID NO.: 1 having at least one substitution selected from the group consisting of leucine at position 10 is substituted with proline, proline at position 15 is substituted with glutamic acid, aspartic acid at position 44 is substituted with asparagine, leucine at position 45 is substituted with valine, leucine at position 45 is substituted with isoleucine, glutamine at position 56 is substituted with histidine, phenylalanine at position 60 is substituted with leucine, phenylalanine at position 60 is substituted with valine, arginine at position 97 is substituted with lysine, arginine at position 109 is substituted with lysine, aspartic acid at position 123 is substituted with glycine, histidine at position 156 is substituted with aspartic acid, alanine at position 157 is substituted with proline, arginine at position 240 is substituted with serine, glycine at position 244 is substituted with tryptophan, glycine at position 244 is substituted with arginine, glutamine at position 249 is substituted with histidine, alanine at position 268 is substituted with valine and serine at position 271 is substituted with proline.

Yet further, the presently described subject matter provides an IL17RA-ECD mutant having at least two substitutions.

In addition, the presently described subject matter provides an IL17RA-ECD mutant having seven or less substitutions.

The presently described subject matter provides an IL17RA-ECD mutant, comprising or consisting of, the amino acid sequence of SEQ ID NO: 4 or the amino acid sequence of SEQ ID NO: 11.

The presently described subject matter further provides an IL17RA-ECD mutant comprising or consisting of the amino acid sequence of SEQ ID NO: 4.

The presently described subject matter yet further provides an IL17RA-ECD mutant comprising or consisting of the amino acid sequence of SEQ ID NO: 11.

The presently described subject matter also provides an isolated peptide, comprising or consisting of the amino acid sequence of a presently described IL17RA-ECD mutant.

The presently described subject matter provides an isolated peptide, comprising or consisting of an amino acid sequence of an IL17RA-ECD mutant having at least 90% homology with the amino acid sequence of SEQ ID: NO 1.

Further, the presently described subject matter provides an isolated peptide, comprising or consisting of an amino acid sequence of an IL17RA-ECD mutant having at least 95% homology with the amino acid sequence of SEQ ID: NO 1.

Still further, the presently described subject matter provides an isolated peptide, comprising or consisting of an amino acid sequence of an IL17RA-ECD mutant having at least 99% homology with the amino acid sequence of SEQ ID: NO 1.

The presently described subject matter provides an isolated nucleic acid molecule encoding an IL17RA-ECD mutant according to the presently described subject matter.

The presently described subject matter also provides an expression vector comprising the nucleic acid molecule encoding an IL17RA-ECD mutant according to the presently described subject matter.

The presently described subject matter further provides an isolated host cell transformed or transfected with the presently described expression vector, enabling the host cell to express the presently described IL17RA-ECD mutant.

In addition, the presently described subject matter provides an isolated host cell transformed or transfected with the presently described expression vector, enabling the host cell to express the presently described IL17RA-ECD mutant, wherein the host cell is a mammalian cell.

Yet further, the presently described subject matter provides a pharmaceutical composition, comprising or consisting of the presently described IL17RA-ECD mutant or the presently described isolated peptide; and a pharmaceutically acceptable carrier or diluent.

In addition, the presently described subject matter provides a pharmaceutical composition as presently described, formulated in a dosage form selected from the group consisting of an intravenous dosage form and a subcutaneous dosage form.

The presently described subject matter provides a pharmaceutical composition comprising or consisting of the presently described IL17RA-ECD mutant or the presently described isolated peptide; a pharmaceutically acceptable carrier or diluent; and at least one anti-inflammatory agent.

The presently described subject matter further provides a method of treating inflammation or an inflammatory disorder in a subject, comprising or consisting of, administering to the subject in need thereof a therapeutically effective amount of an IL17RA-ECD mutant, pharmaceutical composition, or isolated peptide, according to the presently described subject matter.

The presently described subject matter yet further provides a method of treating inflammation or an inflammatory disorder in a subject, wherein administering comprises intravenous administration or subcutaneous administration.

The presently described subject matter also provides a method of treating inflammation or an inflammatory disorder in a subject, comprising or consisting of, administering to the subject in need thereof a therapeutically effective amount of an IL17RA-ECD mutant, pharmaceutical composition, or isolated peptide, according to the presently described subject matter; and administering a therapeutically effective amount of at least one anti-inflammatory agent.

In addition, the presently described subject matter provides a method of treating inflammation or an inflammatory disorder wherein the at least one anti-inflammatory agent is selected from the group consisting of a corticosteroid, cortisol; aldosterone, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, flucinonide, fluocinolone acetonide, halcinonide, betamethasone, betamethasone sodium phosphate, dexamethasone, dexamethasone dodium phosphate, flucortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, flucortolone caproate, fluocortolone pivalate, fluprednidene acetate, a non-steroidal anti-inflammatory, a cox-2 inhibitor, nimesulide, diclofenac, licofelone, aspirin, ibuprofen, naproxen, an immune selective anti-inflammatory derivative, phenylalanine-glutamine-glycine, an herb, Harpagophytum, hyssop, ginger, turmeric, *Arnica Montana*, willow bark, —*cannabis*, and any combination thereof.

Further, the presently described subject matter provides a method of treating inflammation or an inflammatory disorder in a subject, wherein the at least one anti-inflammatory agent is administered simultaneously with, before, or after administration of the IL17RA-ECD mutant, the pharmaceutical composition, or the isolated peptide.

Yet further, the presently described subject matter provides a method of treating inflammation or an inflammatory disorder in a subject, comprising or consisting of, administering to the subject in need thereof a therapeutically effective amount of the presently described pharmaceutical composition.

In addition, the presently described subject matter provides a method of treating inflammation or an inflammatory disorder in a subject, comprising or consisting of administering to the subject in need thereof a therapeutically effective amount of an isolated peptide or a pharmaceutical composition comprising the isolated peptide, according to the presently described subject matter.

The presently described subject matter provides a method of inhibiting hIL-17A induced secretion of IL-6 and/or CXCL1 and/or TNF-α in a cell or population of cells, comprising or consisting of administering to the cell or population of cells, an amount of the presently described IL17RA-ECD mutant, pharmaceutical composition, or isolated peptide, effective to inhibit hIL-17A induced secretion of IL-6 and/or Gro-α.

Further, the presently described subject matter provides a method of inhibiting hIL-17A induced secretion of IL-6 in a cell or population of cells, comprising or consisting of administering to the cell or population of cells, an amount of the presently described IL17RA-ECD mutant, pharmaceutical composition, or isolated peptide, effective to inhibit hIL-17A induced secretion of IL-6.

Yet further, the presently described subject matter provides a method of inhibiting hIL-17A induced secretion of IL-6 and/or CXCL1, in cells of a subject, comprising or consisting of administering to the subject an amount of the presently described IL17RA-ECD mutant, pharmaceutical composition, or isolated peptide, effective to inhibit hIL-17A induced secretion of IL-6 and/or CXCL1.

Still further, the presently described subject matter provides a method of inhibiting hIL-17A induced secretion of IL-6 and/or CXCL1, in cells of a subject suffering from inflammation or an inflammatory disorder, comprising or consisting of administering to the subject an amount of the presently described IL17RA-ECD mutant, pharmaceutical composition, or isolated peptide, effective to inhibit hIL-17A induced secretion of IL-6 and/or CXCL1, and reduce symptoms of inflammation.

The presently described subject matter provides a method of inhibiting hIL-17A induced secretion of IL-6 and/or CXCL1, wherein the cell is a mammalian cell.

The presently described subject matter also provides a method of inhibiting hIL-17A induced secretion of IL-6 and/or CXCL1, wherein the mammalian cell is a human cell.

The presently described subject matter further provides a method of treating inflammation or an inflammatory disorder in a subject, comprising or consisting of, inhibiting hIL-17A induced secretion of one or more of TNF-α, IL-6, and CXCL1, in cells of the subject comprising administering to the subject an amount of the presently described IL17RA-ECD mutant, pharmaceutical composition, or isolated peptide, effective to inhibit hIL-17A induced secretion of one or more of TNF-α, IL-6, and CXCL1, and reduce symptoms of inflammation.

BRIEF DESCRIPTION OF THE FIGURES

FIG. 2A is a Schematic representation of hIL17RA displayed on the yeast cell surface.

FIG. 2B is graphical representation of expression of hIL17RA-ECD relative to yeast PCNA and a negative control cells using YSD.

DETAILED DESCRIPTION

Definitions

Figure 1:
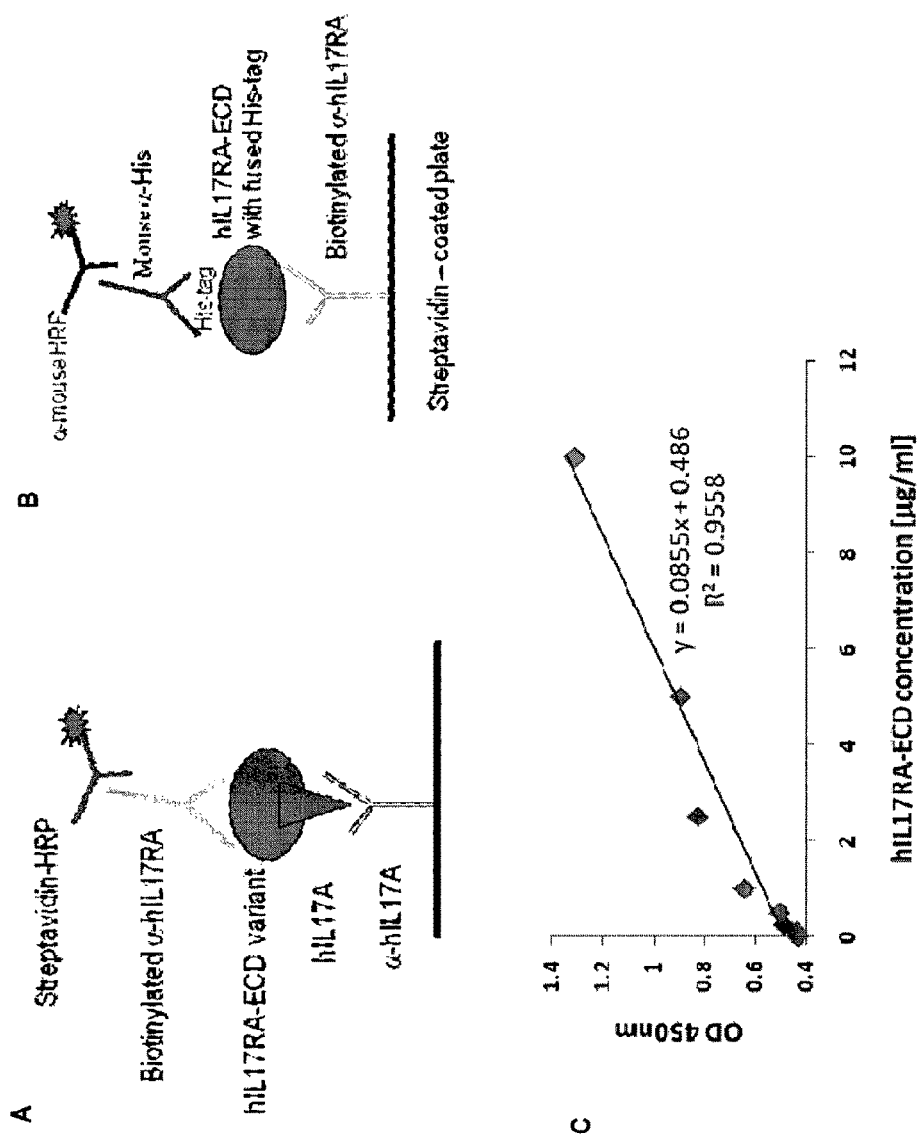
FIG. 1A depicts an ELISA for hIL-17RA binding to hIL-17A.
FIG. 1B depicts an ELISA for hIL-17RA specific expression in *E. coli* cells.
FIG. 1C is a graphical representation of a hIL17RA-ECD calibration curve.

The below definitions serve to provide a clear and consistent understanding of the specification and claims, including the scope to be given such terms.

As used herein, the phrases "active agent," "drug product," "pharmaceutical composition," "pharmaceutical dosage form," and the like, refer to the combination of one or more active agents, for example, one or more of the presently described IL17RA mutant peptides, and optionally one or more excipients, that is administered to a patient in need of treatment, and can be in any desired form, including for example, in the form of a solution, an aqueous solution, an emulsion, and a suspension.

Pharmaceutical compositions containing a presently described peptide as the active ingredient can be prepared according to conventional pharmaceutical compounding techniques. See, for example, *Remington's Pharmaceutical Sciences*, 18th Ed., Mack Publishing Co., Easton, Pa. (1990). See also, *Remington: The Science and Practice of Pharmacy*, 21st Ed., Lippincott Williams & Wilkins, Philadelphia, Pa. (2005). Suitable formulations can include, but are not limited to, injectable formulations including for example, solutions, emulsions, and suspensions. The compositions contemplated herein may take the form of solutions, suspensions, emulsions, combinations thereof, or any other pharmaceutical dosage form as would commonly be known in the art.

As used herein, the terms "administering," "administration," and like terms refer to any method which, in sound medical practice, delivers a composition containing an active agent to a subject in such a manner as to provide a therapeutic effect. One aspect of the present subject matter provides for oral administration of a therapeutically effective amount of a composition of the present subject matter to a patient in need thereof. Other suitable routes of administration can include parenteral, subcutaneous, intravenous, intramuscular, or intraperitoneal. The dosage administered will be dependent upon the age, health, and weight of the recipient, kind of concurrent treatment, if any, frequency of treatment, and the nature of the effect desired.

As used herein, the term "carrier," "excipient," or "adjuvant" refers to any component of a pharmaceutical composition that is not the active agent.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

Each of the terms "Gro-α," "keratinocyte-derived chemokine (KC)," and "CXCL1," refer to a small cytokine belonging to the CXC chemokine family CXCL1 is expressed by macrophages, neutrophils and epithelial cells, and has neutrophil chemoattractant activity. In humans, this protein is encoded by the CXCL1 gene.

The term "homology" refers to the percent of identity between two polynucleotide or two peptide moieties. The correspondence between the sequence from one moiety to another can be determined by techniques known to the art. For example, homology can be determined by a direct comparison of the sequence information between two peptide molecules by aligning the sequence information and using readily available computer programs.

In an embodiment, two amino acid sequences are "substantially homologous" or "substantially similar" when at least about 50%, at least 60%, at least 70%, at least 80%, at least 85%, at least 90%, at least 92%, at least 93%, at least 94%, at least 95%, at least 96%, at least 97%, at least 98%, or at least 99%, of the amino acids match over the defined length of the sequences. Sequences that are substantially homologous can be identified by comparing the sequences using known techniques.

The term "hIL-17A" as used herein, refers to a proinflammatory cytokine that is expressed by a unique lineage of CD4 T cells (Th-17) and is known to stimulate fibroblasts, endothelial, epithelial cells and macrophages to produce multiple proinflammatory mediators.

The term "hIL-17RA" as used herein refers to the presently described engineered soluble hIL-17RA receptors with high affinity to hIL-17 that inhibit downstream IL17A induced signaling events in cells. The presently described engineered soluble hIL-17RA receptors exhibit increased binding affinity to hIL17A relative to the wild type (WT) IL17RA soluble receptor. Such increased affinity of hIL-17RA to hIL17A relative to (WT) IL17RA can be from two-fold to ten-fold, from three-fold to eight-fold, from three-fold to six-fold, from four-fold to six-fold, from 5-fold to six-fold, about two-fold, about three-fold, about four-fold, about five-fold, about six-fold, about seven-fold, or about eight-fold higher.

The term "IL17RA-ECD" as used herein, refers to the hIL-17RA extra cellular domain (ECD).

As used herein, the phrase "IL17RA-ECD mutant" or "IL17RA-ECD variant" or "peptide" refers to a mutant or variant of the wild type (WT) hIL17RA-ECD (SEQ ID NO: 1) (human), peptide having at least about 90% homology to the WT IL17RA, about 91% homology, about 92% homology, about 93% homology, about 94% homology, about 95% homology, about 96% homology, about 97% homology, about 98% homology, or about 99% homology to the WT IL17RA-ECD. The presently described IL17RA-ECD mutant can exhibit a higher specific IL17RA-ECD activity towards IL-17A than the wild-type hIL17RA-ECD whose amino acid sequence is SEQ ID NO: 1. Such increased specific activity of IL-17RA-ECD to hIL17A relative to (WT) IL17RA-ECD can be from two-fold to ten-fold, from three-fold to eight-fold, from three-fold to six-fold, from four-fold to six-fold, from 5-fold to six-fold, about two-fold, about three-fold, about four-fold, about five-fold, about six-fold, about seven-fold, or about eight-fold, higher. Such IL17RA-ECD mutants or variants include those having the amino acid sequence of SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; and SEQ ID NO: 85. The described IL17RA-ECD mutants are more thermostable than the WT IL17RA soluble receptor, and thus, exhibit higher stability during long storage periods at room temperature. For example, the presently described mutants are stable and active at temperatures from >50° C. to 70° C., from >50° C. to 65° C., from >50° C. to 62° C., from 55° C. to 65° C., from 55° C. to 62° C., from >55° C. to at least 60° C., from >56° C. to at least 60° C., from >58° C. to at least 60° C., from 58° C. to 65° C., from 58° C. to 62° C., from 59° C. to 61° C., or at about 60° C.

The term "inflammation" as used herein refers to inflammation characterized by a statistically significant increase in the systemic concentration of one or more cytokines, including for example, TNF-α, CXCL1 and/or IL-6, as compared to the levels of TNF-α, CXCL1, and/or IL-6, expected in a normal, healthy population matched on the basis of, for example, one or more of age, body mass index, gender, smoking status, and ethnicity. For example, a median concentration of IL-6 observed in a normal, healthy Caucasian population is about 1.47 pg/ml, and about 2.89 pg/ml for TNF-α.

The phrase "inflammatory disorder" as used herein refers to any disease or disorder characterized by inflammation, for example, involving hIL-17A.

The term "inhibiting" or "inhibit" as used herein, refers to a statistically significant reduction in the concentration, for example, systemic concentration, of one or more cytokines including, for example, TNF-α, CXCL1, and/or IL-6, observed in response to administering the presently described IL-17RA-ECD mutant, peptide, or pharmaceutical composition, as presently described, to a cell, a population of cells, or a subject, as compared to the concentration observed in the cell, population of cells, or subject, prior to administration.

The term "isolated" as used herein designates a biological material (nucleic acid or protein) that has been removed from its original environment (the environment in which it is naturally present). For example, a peptide present in the natural state in a plant or an animal is not isolated; however, the same peptide separated from the adjacent amino acids in which it is naturally present, is considered "isolated."

As used herein the term "peptide" means a compound that is made up of two or more amino acids joined by covalent bonds which are formed by the elimination of a molecule of H₂O from the amino group of one amino acid and the carboxyl group of the next amino acid.

As used herein, the term "pharmaceutically acceptable carrier" refers to a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present.

Any non-toxic, inert, and effective carrier may be used to formulate the compositions contemplated herein. Suitable pharmaceutically acceptable carriers, excipients, and diluents in this regard are well known to those of skill in the art, such as those described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO.

These additional inactive components, as well as effective formulations and administration procedures, are well known in the art and are described in standard textbooks, such as *Goodman and Gillman's: The Pharmacological Bases of Therapeutics*, 8th Ed., Gilman et al. Eds. Pergamon Press (1990); *Remington's Pharmaceutical Sciences*, 18th Ed., Mack Publishing Co., Easton, Pa. (1990); and *Remington: The Science and Practice of Pharmacy*, 21st Ed., Lippincott Williams & Wilkins, Philadelphia, Pa., (2005), each of which is incorporated by reference herein in its entirety.

The presently described mutants, variants or peptides may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, *Current Protocols in Protein Science*, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

The term "purified" does not require the material to be present in a form exhibiting absolute purity, exclusive of the presence of other compounds. Rather, it is a relative definition. A peptide is in the "purified" state after purification of the starting material or of the natural material by at least one order of magnitude, 2 or 3, or 4 or 5 orders of magnitude.

The term "substantially free of naturally-associated host cell components" describes a peptide or other material which is separated from the native contaminants which accompany it in its natural host cell state. Thus, a peptide which is chemically synthesized or synthesized in a cellular system different from the host cell from which it naturally originates will be free from its naturally-associated host cell components.

As used herein, the term "substantially pure" describes a peptide or other material which has been separated from its native contaminants Typically, a monomeric peptide is substantially pure when at least about 60 to 75% of a sample exhibits a single peptide backbone. Minor variants or chemical modifications typically share the same peptide sequence. A substantially pure peptide can comprise over about 85 to 90% of a peptide sample, and can be over 95% pure, over 97% pure, or over about 99% pure. Purity can be measured on a polyacrylamide gel, with homogeneity determined by staining. Alternatively, for certain purposes high resolution may be necessary and HPLC or a similar means for purification can be used. For most purposes, a simple chromatography column or polyacrylamide gel can be used to determine purity.

The term "sequence similarity" in all its grammatical forms refers to the degree of identity or correspondence between nucleic acid or amino acid sequences of proteins that may or may not share a common evolutionary origin. See Reeck et al., 1987, Cell 50: 667.

The active agent is preferably administered in a "therapeutically effective amount." As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the presently described manner. The phrase "therapeutically effective amount" as used herein refers to an amount of the presently described active agent effective to yield a desired therapeutic response. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington: The Science and Practice of Pharmacy*, 21st Ed., Lippincott Williams & Wilkins, Philadelphia, Pa., (2005).

As used herein, the terms "subject" or "individual" or "animal" or "patient" or "mammal," refers to any subject, particularly a mammalian subject, for whom diagnosis, prognosis, or therapy is desired, for example, a human.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "prevention" of a disease, disorder, or condition encompasses the delay, prevention, suppression, or inhibition of the onset of a disease, disorder, or condition. The presently described peptides, including vaccine compositions, may be utilized for purposes of preventing, suppressing or treating inflammatory disorders described herein. As used in accordance with the presently described subject matter, the term "prevention" relates to a process of prophylaxis in which a subject is exposed to the presently described peptides prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Other terms as used herein are meant to be defined by their well-known meanings in the art.

Methods of Producing IL17RA-ECD Mutants

The presently described peptides can be prepared by chemical synthesis, or may be manufactured using recombinant DNA technology. To prepare the presently described peptides by chemical synthesis, publicly known methods may be used, for example, the presently described peptides can be obtained by methods using azide, acid chloride, acid anhydride, compound acid anhydride, DCC, activated ester, Woodward's reagent K, carbonylimidazole, deoxidization, DCC/HONB, BOP reagent (see for example Bozanszky, M and M. A. Ondetti, *Peptide Synthesis*, Interscience Publishers, New York (1966); Schroeder and Luebke, *The Peptide*, Academic Press, New York (1965); F. M. Finn and K. Hofinann, *The Proteins* Vol. 2, H. Nenrath, R. L. Hill ed., Academic Press Inc., New York (1976); Nobuo Izumiya et al., Peptide Gosei no Kiso to Jikken (*Basics and experiments of peptide synthesis*), Maruzen Co. (1985); Haruaki Yajima and Shunpei Sakakibara et al., Seikagaku Jikken Koza (*Biochemical Experiment*) 1, Japanese Biochemical Society ed., Tokyo Kagaku Dojin Co. (1977); Toshiya Kimura, Zoku Seikagaku Jikken Koza (*Sequel to Biochemical Experiment*) 2, Japanese Biochemical Society ed., Tokyo Kagaku Dojin Co. (1987)). Furthermore, the presently described peptide can be prepared by chemical synthesis using an automated peptide synthesizer (e.g. PE Applied Bio Systems Co.). Methods, such as those described in Bulaj G., et al. (2006) Biochemistry 45, 7404, can also be used for synthesis of the presently described peptides and refolding procedures.

Further, following the completion of reaction, the presently described peptides can be purified and separated by publicly known purification methods. For example, the presently described peptides can be purified and separated by a combination of solvent extraction, distillation, column chromatography, liquid chromatography, recrystallization and the like. Where the presently described peptides obtained by the above methods are in a free form, publicly known methods can be used to convert it into a salt form, and on the other hand, where the peptide is obtained in a salt form, publicly known methods can be used to convert it into a free form.

In addition, recombinant expression systems may be used to express the presently described peptides.

Other Biological Methods

Methods involving conventional and analytical chemistry, molecular biological and cell biological techniques are described herein. Such techniques are generally known in the art and are described in detail in methodology treatises such as *Classics in Total Synthesis, Targets, Strategies, Methods*, K. C. Nicolaou and E. J. Sorensen, VCH, New York, 1996; *The Logic of Chemical Synthesis*, E. J. Coney and Xue-Min Cheng, Wiley & Sons, NY, 1989; and *NMR of Proteins and Nucleic Acids*, Wuthrich, K., Wiley & Sons, New York, 1986. Molecular biological and cell biological methods are described in treatises such as *Molecular Cloning: A Laboratory Manual*, 3rd ed., vol. 1-3, ed. Sambrook et al., Cold Spring Harbor Laboratory Press, Cold Spring Harbor, N.Y., 2001; and *Current Protocols in Molecular Biology*, ed. Ausubel et al., Greene Publishing and Wiley-Interscience, New York, 1992 (with periodic updates).

Pharmaceutical Compositions Including IL17RA-ECD Mutants

Formulation

The presently described pharmaceutical compositions can be administered systemically or locally. They can be given in forms suitable for each administration route. For example, they can be administered by infusion or injection, including for example, intravenous and subcutaneous.

Details of general formulation procedures and information on additional excipients may be found in Remington: *The Science and Practice of Pharmacy*, 21st Edition.

A composition containing an effective amount of the peptides described herein can be administered to a subject requiring treatment.

The composition of the treatment may formulated to be compatible with the route of administration. The composition can be formulated, for example, as a solution. See, e.g., *Journal of Pharmaceutical Sciences*, (1963), 52:918 et seq.

A solution for parenteral, intradermal, or subcutaneous administration may comprise, for example: a sterile diluent such as water, saline, glycerin, fixed oils, polyethylene glycols, propylene glycol, or other synthetic solvents; an antibacterial agents such as benzyl alcohol or methyl parabens; an antioxidant such as ascorbic acid or sodium bisulfite; a chelating agent; a buffering agent such as acetate or phosphate. The solution can be stored in ampoules, disposable syringes, or plastic or glass vials.

A formulation for injection or intravenous administration can include a carrier which is a solvent or a dispersion medium. Suitable carriers include water, physiological saline, bacteriostatic water, Cremophor EL™ (BASF, Parsippany, N.J.) phosphate buffered saline (PBS), ethanol, polyols (e.g., glycerol, glycol, propylene glycol, and the like), and mixtures thereof. These compositions must be sterile and fluid to allow injection. Fluidity can be maintained with a coating such as lecithin or a surfactant. Microbial contamination can be prevented by the inclusion of antibacterial and antifungal agents, such as parabens, chlorobutanol, phenol, ascorbic acid, and thimerosal. Sugars and polyalcohols, such as manitol, sorbitol, sodium chloride, can be used to maintain isotonicity in the composition.

Sterility can be insured by filter sterilization of the solution. Alternatively, the solution can be produced from components that were individually filter-sterilized. A filter-sterilized component can be vacuum dried or freeze dried to produce a sterile powder. Such a powder can be rehydrated prior to injection with a sterile carrier solution.

Suitable formulations can include, for example, the presently described mutants or variants in a vehicle of glycerol and buffer, including for example, in 30% glycerol in 50 mM Tris, 200 mM NaCl, pH7.5.

Modes of Administration

The presently described compositions, mutants, variants and peptides, described herein can be administered, for example, by bolus injection, by continuous infusion, for example, so as to prolong contact with the epidural region or by other known methods. The compositions, mutants, variants or peptides can be infused for any amount of time. Dosage and timing of administration can be modified according to the needs of the particular subject, e.g., within the framework of standard clinical protocols for treating pain. The compositions, mutants, variants or peptides can also be delivered by intrathecal routes, and into the bloodstream. In addition, implantable or body-mountable pumps can be used to deliver the compositions, mutants, variants or peptides described herein at a controlled rate. Alternatively, prolonged administration can be achieved by art-known depot or sustained release formulations.

Dosage

An appropriate dosage for treatment must be determined. An effective amount of the presently described compositions, mutants, variants or peptides is the amount or dose which is required to ameliorate a symptom in a subject.

Determination of the amount or dose required to treat an individual subject is routine to one skilled in the art, e.g., a physician, pharmacist, or researcher.

The toxicity and therapeutic efficacy of the presently described composition, mutant, variant or peptide formulations may also be determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Suitable ratios include, for example, rations greater than about 2, 5, 10, 50, or 100. Compounds, formulations, and methods of administration with high therapeutic indices can be determined, as such treatments have little toxicity at dosages which provide high efficacy.

In formulating a dosage range for use in humans, the effective dose of presently described compositions, mutants, variants or peptides can be estimated from studies with laboratory animals. A dose can be formulated in an animal in order to achieve a desired circulating plasma concentration of peptide. An exemplary dose produces a plasma concentration which exceeds the $IC_{50}$ (i.e., the concentration of the test compound which achieves a half-maximal inhibition of a symptom) as determined in cell culture assays. The circulating plasma concentration can be determined, for example, by obtaining a blood sample, and by analyzing the sample using an antibody based specific ELISA assay or with high performance liquid chromatography or mass spectroscopy.

Alternatively, the dose can be estimated from tests in an animal model, as described below. Alleviation of symptoms is observed when rats receive a peptide or pharmaceutical composition at a dose of at least about from 1 μg/kg to 25 mg/kg, from 1 mg/kg to 10 mg/kg, from 10 mg/kg to 25 mg/kg, or more. The interrelationship of dosages for animals and humans (based on milligrams per meter squared of body surface) is described by, for example, Freireich et al., *Cancer Chemother. Rep.* 1966, 50, 219. Body surface area may be approximately determined from height and weight of the patient. See, e.g., Scientific Tables, Geigy Pharmaceuticals, Ardley, N.Y., 1970, 537. See also, *Principles and Practice of Pharmaceutical Medicine*, Lionel D. Edwards, Andrew J. Fletcher, Anthony W. Fox and Peter D. Stonier, (2007). The presently described compositions, mutants, variants or peptides can be administered with a frequency or continuously in order to maintain a local concentration effective to treat an inflammatory and/or autoimmune disorder.

Depending on the method of administration, the appropriate dose can vary. The dose for a patient can be optimized while the patient is under care of a physician, pharmacist, or researcher. For example, a relatively low dose of the compositions, mutants, variants or peptides described can be administered initially. The patient can be monitored for symptoms. The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

EXAMPLES

Materials and Methods
Plasmids hIL-17RA EST clone was purchased from Open Biosystems. For *E. coli* expression, the ECD of the gene was cloned into pET32 plasmid (Novagen). The cloning was performed using NcoI and NotI sites to yield a Thioredoxin (Trx)-6× Histidine-tagged version of the protein. *E. coli* Clooni strain (Lucigen) was used for cloning and plasmid extraction. For yeast surface display, the variants were cloned into pCT-CON plasmid using the NheI and BamHI sites (Chao, G. et al. *Nat. Protocols* 1, 755-768 (2006)). For expression in mammalian cells, the pFUSE (Invivogen), pFW02 (Crown-Bio) and pYD11 (CrownBio) vectors were used, to yield hIL17RA-ECD variant fused with human IgG1 engineered Fc, with greatly reduced antibody-dependent cellular cytotoxicity (ADCC) and complement dependent cytotoxicity (CDC). Primers used for the cloning and library construction are listed in Table 1.

TABLE 1

List of Primers.

| Primer name | 5' → 3' sequence | SEQ ID NO. |
|---|---|---|
| Primers for hIL17RA-ECD | | |
| ECD-nested-Not | GTGGTGGTGGTGGTGCTC | 38 |
| ECD-nested-Nco | GTACCGACGACGACGACAAG | 39 |
| fr-pCTCON-ECD IL17RA | ATAAACGCTAGCTCCCTGCGACTCCTG GACCACC | 40 |
| rev-pCTCON-ECD IL17RA | TAGATGTCGGATCCGTACACCCACAGG GGCATGTAGTCC | 41 |
| fr-pCTCON-ECD hr | GGTGGTGGTTCTGGTGGTGGTGGTTCT GGTGGTGGTGGTTCTGCTAGCTCCCTG CGACTCCTGGACCACC | 42 |
| rev-pCTCON-ECD hr | GATCTCGAGCTATTACAAGTCCTCTTC AGAAATAAGCTTTTGTTCGGATCCGTA CACCCACAGGGGCATGTAGTCC | 43 |
| fr-ECD | TCCCTGCGACTCCTGGACCACC | 44 |
| rev-ECD | GTACACCCACAGGGGCATGTAGTCC | 45 |
| fr-pET$_{32}$-ECD/Nco | ATTCGATGCCATGGCCTCCCTGCGACT CCTGGACCACC | 46 |
| rev-pET$_{32}$-ECD/Not | TCACTCAGTGCGGCCGCCTATTAGTAC ACCCACAGGGGCATGTAGTCCG | 47 |
| fr-ECD-Nco-pFC | CCATGGTTCTGCGACTCCTGGACCACC GGGCGCTG | 48 |
| rev-ECD-Xba-pFC | TCTAGACCACAGGGGCATGTAGTCCG | 49 |
| fr-ECD-Bam-pFC | GGATCCTAGAGAGGCTTGTGGGGCCTC AGG | 50 |
| rev-ECD-SalI-pFC | GTCGACGCCCACAGGGGCATGTAGTCC GG | 51 |
| Primers for mutants library | | |
| L10P | TGGACCACCGGGCGCCGGTCTGCTCCC AGCC | 52 |
| P15E | CTGGTCTGCTCCCAGGAAGGGCTAAAC TGCACG | 53 |
| D44N | CCTCCTCCCCAAAGAACCTGCAGATCC AGC | 54 |
| L45I | TCCTCCCCAAAGGACATTCAGATCCAG CTGCAC | 55 |

TABLE 1-continued

List of Primers.

| Primer name | 5' → 3' sequence | SEQ ID NO. |
|---|---|---|
| L45V | CTCCTCCCCAAAGGACGTGCAGATCCAGCTGC | 56 |
| Q56H | CCCACACCCAACATGGAGACCTGTTCCC | 57 |
| F60V | CAACAAGGAGACCTGGTGCCCGTGGCTCACATC | 58 |
| F60L | CAACAAGGAGACCTGCTGCCCGTGGCTCACATC | 59 |
| R97K | CGTTTGTGCGTCAAATTTGAGTTTCTGTCC | 60 |
| R109K | TGAGGCATCACCACAAACGGTGGCGTTTTACC | 61 |
| D123G | GTGGTTGACCCTGGCCAGGAATATGAGGTG | 62 |
| H156D | GTGCCTGACTGTGAGGATGCCAGGATGAAGG | 63 |
| A157P | CTGACTGTGAGCATCCGAGGATGAAGGTAACC | 64 |
| R240S | CACACTCACTCTAAGCAACCTTAAAGGGTG | 65 |
| G244W | ACGCAACCTTAAATGGTGCTGTCGCCACC | 66 |
| Q249H | GTGCTGTCGCCACCATGTGCAGATCCAGC | 67 |
| A268V | GCCTCAGACACTCCGTGACTGTTTCCTGCCC | 68 |
| S271P | CACTCCGCGACTGTTCCGTGCCCAGAAATGCC | 69 |

Primers for sequence

| fr-pET$_{32}$-seq | TTCCTCGACGCTAACCTGGCC | 70 |
| rev-pET$_{32}$-seq | AGCAGCCGGATCTCAGTGGTGG | 71 |
| fr-pCTCON-lib | GACGATTGAAGGTAGATACCCATACGACGTTCC | 72 |
| rev-pCTCON-lib | CAGATCTCGAGCTATTACAAGTCCTCTTCAG | 73 |
| pFC-fr | GTTTTCTGTTCTGCGCCGTTAC | 74 |
| pFC-rev | GCATTCTAGTTGTGGTTTGTCC | 75 |
| pFC-rev-in | CATGAGGGTGTCCTTGGGTTTTGG | 76 |

Yeast Surface Display hIL17RA-ECD variants were displayed on the yeast cell surface of EBY100 strain cells (see Chao, G. et al. (2006) for genotype) and analyzed by flow cytometry, essentially as described by Chao, G. et al. (2006). Briefly, EBY100 transformed with plasmid pCTCON containing the desired clone were grown in SDCAA media (20 g sucrose, 6.7 g yeast nitrogen base, 5 g casamino acids, 5.4 g Na$_2$HPO$_4$ and 8.56 g NaH$_2$PO$_4$*H$_2$O) to logarithmic phase, then 2*10$^6$ of cells were washed, resuspended in SGCAA induction media (similar to SDCAA but containing galactose instead of sucrose) and grown at 37° C. with shaking for an additional 18 hours. Induced cells (1*10$^6$) were collected by centrifugation, washed with PBSF (PBS+1 g/L BSA) and incubated for 1 hour at 25° C. with 0.2 μM hIL-17A (R&D Systems). The cells were then washed and incubated for 1 hour at 25° C. with mouse α-Myc antibodies (Santa Cruz Biotechnology, 1 μl/50 μl PBSF) and goat biotinilated α-hIL-17A (R&D Systems, 0.25 μl/50 μl PBSF). Subsequently, cells were washed again and incubated with fluorescein isothiocyanate (FITC) conjugated α-mouse IgG (Sigma, 1 μl/50 μl PBSF) and allophycocyanin (APC) conjugated streptavidin (Jackson Immunoresearch, 1 μl/50 μl PBSF) for an additional 1 hour on ice, with frequent mixing. The labeled cells were washed, resuspended with PBSF and analyzed by fluorescence activated cell sorting (FACS Calibur, BD). The positive control proliferating cell nuclear antigen (PCNA) gene was expressed and displayed on the yeast cell surface under identical conditions.

Mutant Library Generation hIL17RA-ECD "back to consensus" library was generated by targeting specific residues that deviate from the family consensus. Based on the alignment of the hIL17RA-ECD with IL17RA-ECD from other mammalians, we found 18 positions that deviated from the consensus sequence. hIL17RA-ECD gene was amplified by PCR, and ~10 μg were digested with DNaseI to yield 50-125 bp fragments as described in Stemmer, W. P. (1994). The fragments were reassembled, as in DNA shuffling (Aharoni, A. et al. 2004) in the presence of a mixture of 18 short oligos (4-6 nM each, Table 1), resulting in a library containing 2-6 mutations in each gene (Stemmer, W. P. 1994). The reaction mixture was further amplified by nested PCR as described in Chao, G. et al. (2006). The assembled libraries were ligated into pET32 vector for E. coli expression and into the pCTCON vector for yeast surface display. This naïve mutations library was transformed to yeast and displayed on the yeast surface (Chao, G. et al. 2006). The same library was also directly cloned into pET32 plasmid, expressed in E. coli and screened for mutants with higher expression level than that of the original clone, as described above.

Library Selection Using Yeast Surface Display

The naïve library was induced and labeled with c-myc and hIL-17A, as described above. EBY100 cells (1*10$^7$) displaying the hIL-17RA library were labeled, analyzed and sorted using a FACS (Vantage, BD). Two to three iterative rounds of enrichment were performed. In each round, multiple 'positive' events (3-5*10$^4$), corresponding to cells found within the top 1-2% of the green and red fluorescence intensity area, were collected into growth media and plated on agar for a new round of enrichment. For initial sorting of the naïve library, a sort gate of the top 5% of fluorescent cells was used. Selection rounds were continued until no further enrichment was obtained.

Cloning and Bacterial Expression of hIL17RA-ECD Variants

A pool of plasmids from the last round of FACS enrichment was PCR-amplified, cloned into plasmid pET32 and transformed to E. coli BL21 (DE3) strain (Novagen). Alternately, plasmids of the naïve libraries were transformed to BL21 E. coli cells. Following transformation, single colonies were inoculated into 10 ml LB media containing 100 μg/ml ampicillin, grown to OD$_{600}$ of 0.6 and induced with 1 mM of IPTG (Calbiochem) overnight at 30° C. The cells were then harvested, lysed in PBS supplemented with 0.2% Triton, 200 μg/ml lysozyme (Calbiochem) and 10 mM β-mercaptoethanol, centrifuged and the cleared supernatant was collected and analyzed by ELISA (see below). In each round of selection 140-200 mutants were screened to identify clones with improved activity relative to the WT protein.

Protein Expression in Mammalian Cells

For large scale purification of hIL17RA-ECD variants, HEK293F cells were transiently transformed with 1 μg/ml of DNA dosage and DNA/PEI ratio of 1:3 or 1:4, and harvested after 6-7 days. The recombinant proteins were purified on HiTrap Protein A HP column, with 20 mM sodium phosphate pH 7.0 as binding buffer and 100 mM sodium citrate pH 3.0 as elution buffer. The proteins were then analyzed by silver stain and western blot using specific antibodies against the Fc. Endotoxin concentration was also measured. Purified proteins were stored at −80° C. in 50 mM Tris, 200 mM NaCl pH 7.5 for further analysis.

ELISA Assay for hIL-17A Binding

ELISA plates (Griener Microlon 96W) were incubated with 100 μl of 0.5 μg/ml goat α-hIL-17A antibodies (R&D Systems) for 1 hour, washed with PBS supplemented with 0.05% Tween-80 (PBST) and 100 μl of 0.35 μg/ml hIL-17A (R&D Systems or ProSpec Tany TechnoGene Ltd.) were added to the plate for an additional 1 hour. The plates were then washed with PBST and blocked by incubation with 100 μl of PBS supplemented with 3% skim milk for 1 hour. Following blocking, the plates were washed and incubated with 100 μl of the cleared lysate, cell media or purified protein generated (described above) at appropriate dilutions and shaken for 1 hour. hIL-17RA (R&D Systems) was applied at a concentration of 6.25 μg/ml as a positive control, and PBS supplemented with 1% BSA as a negative control. Plates were then washed with PBST, incubated with 100 μl of 0.05 μg/ml goat α-hIL-17RA antibodies (R&D Systems) followed by a secondary peroxidase-conjugated streptavidin (Jackson, 1:10000 dilution). Finally, 100 μl of the horseradish peroxidase (HRP) chromogenic 3,3',5,5'-tetramethylbenzidine (TMB) substrate solution (Dako) were added. The reaction was stopped by the addition of 1 M sulfuric acid and recorded at 450 nm using a Tecan Infinite M200 plate reader.

ELISA Assay for the Detection of hIL17RA Expression in E. coli

ELISA plates (Griener Microlon 96W) were coated with 100 μl of 0.2 μg streptavidin (Pierce) and 100 μl of 0.05 μg/ml goat α-hIL-17RA antibodies (R&D Systems). The plates were then blocked by incubation with PBS supplemented with 3% skim milk for 1 hour. Next, 100 μl of the cleared lysates were added to each well and the plates were incubated with shaking for 1 hour at room temperature. After washing the plates with PBST, the plates were incubated with 100 μl of mouse α-6×His-tag antibodies (Santa-Cruz Biotechnology, 1:2000 dilution), washed with PBST and further incubated with secondary HRP-conjugated goat α-mouse antibodies (Jackson, 1:5000 dilution) for 1 hour. Finally, the HRP chromogenic TMB substrate solution (Dako) was added and the reaction was stopped by the addition of 100 μL of 1M sulfuric acid and recorded at 450 nm using a Tecan Infinite M200 plate reader.

Protein Thermostability

For protein thermostability tests, the purified proteins and commercially available hIL-17RA were diluted in PBS with 1% BSA to a final concentration of 5 μg/ml. The variants were then incubated for 30 min. at different temperatures (ranging from 37 to 70° C.). The reaction was terminated by transferring the proteins to liquid nitrogen, the proteins were kept at −80° C. and then tested for their hIL-17A binding activity by ELISA at room temperature.

Affinity Measurements

The affinity of hIL-17A binding to hIL17RA-ECD variants was determined by SPR measurements on ProteOn XPR36 (Bio-Rad) instrument. All samples were in HBST buffer (10 mM HEPES with 0.15 M NaCl, 3.4 mM EDTA and 0.005% Tween-20, pH 7.2). A GLC Chip was air initialized and activated with EDC/S-NHS and 4 μs from each of the hIL17RA-ECD variants were diluted in Acetate buffer pH 5.5 and immobilized onto the chip. The measured binding levels for WT hIL17RA-ECD, V3 and V10 were ~5300 RU, 6700 RU and 7400 RU, respectively. Following blockage of the unbound sites on the chip with Ethanolamine, the chip was flushed with HBST buffer and rotated. The hIL-17A was run at 25 μl/min. for 300 sec at various concentrations (50, 25, 12.5, 6.25 and 3.125 nM) followed by a 10-min. dissociation step. Binding parameters were determined using Langmuir single binding site model using the Bio-Rad's proteOn Manager Software V2.1.2.05.

Fibroblast-Based Assay for the Inhibition of hIL17 Induced IL6 and Gro-α Secretion Cell line used for the assay is the normal human skin fibroblast cell line ATCC CRL2091. Cells were routinely maintained in completed MEM medium at 37° C. with 5% $CO_2$. Cell cultures for each experiment were allowed to reach 95-100% confluence, counted and checked for viability with 0.5% Trypan Blue solution (Biological Industries). Cells were then diluted to reach $10^5$ cells/ml densities, and 100 μl of the cell suspension are added to each well of 96 well plates (Nunc) to obtain $10^4$ cells per well. The plates were incubated at 37° C. in 5% $CO_2$ for 24 hours until 95-100% confluence was achieved, and then stimulated for additional 24 hours with 10 ng/ml hIL-17A in presence or absence of different amounts of hIL17RA-ECD variants. Dose response of the cell lines to hIL-17A was tested in each experiment by adding different amounts of hIL-17A (0-20 ng/ml). Cell culture supernatants were then collected and stored at −20° C. for further analysis.

Cytokine Detection

Measurement of hIL-6 and hCXCL1 in culture supernatants were performed through the use of ELISA kits (R&D Systems or PeproTech) according to manufacturer description. Standard curves for IL-6 and Gro-α were constructed in each ELISA by adding different amounts of these cytokines (supplied with the kit) instead of the cells supernatant. PeproTech ELISA kit was used with several modifications: briefly, the blocking buffer was PBS supplemented with 3% skim milk, and PBS supplemented with 1% BSA was used as a diluent. The supernatants from cells were diluted 1:5 to 1:10 and used for cytokine detection. The obtained results were converted to pg/ml of IL-6 or CXCL1, according to the respective standard curves.

Example 1

To generate soluble hIL-17R with high affinity for the hIL-17A the focus was on the extracellular domains (ECD) of the hIL-17RA receptor that is known to bind hIL-17A. A directed evolution of hIL-17R for improving stability and binding affinity of hIL17RA-ECD was utilized. First a "back to consensus" library of hIL17RA-ECD was generated and then displayed on the yeast cell surface. The library was enriched for clones that were able to bind hIL17A using flow cytometry. Individual clones from the enriched library were screened using ELISA and several selected hIL-17R variants were overexpressed and purified on a large scale from mammalian cells for further characterization. Finally, pure hIL17RA-ECD variants were tested for binding hIL-17A and inhibition of hIL-17A induced IL-6 and CXCL1 secretion in fibroblast cell line.

Detection of hIL-17A-hIL17-RA Interaction

An ELISA assay was developed for hIL-17RA-hIL-17 interactions in order to facilitate the fast and sensitive screening of a large number of hIL17RA-ECD mutants. The assay is based on immobilizing hIL-17A on ELISA plates and detection of hIL17RA-ECD binding using specific antibodies. To examine the dynamic range for detection of hIL-17RA-hIL17A interaction, varied amounts of the WT hIL17RA-ECD were applied to the plate. Different hIL17RA-ECD concentrations, ranging from 0.1-10 µg/ml, were examined to determine the sensitivity and dynamic range of the ELISA. A solution of 0.35 µg/ml of hIL-17A was used for plate coating to detect hIL17RA-ECD binding following expression in either E. coli or HEK293T cells, and 5-10 µg/ml of the WT hIL17RA-ECD was used as a positive control (FIG. 1). The dependence of the signal on the hIL7RA-ECD concentration was linear and the assay proved to be very sensitive, enabling detection of even low receptor amounts (FIG. 1). In addition, an ELISA assay was developed to directly monitor the hIL17RA-ECD expression level using hIL-17R specific antibodies (FIG. 1). This ELISA assay was used in parallel with the hIL-17A binding ELISA, as an additional tool to estimate hIL17RA-ECD expression level in E. coli.

Yeast Surface Display of hIL17RA-ECD.

A yeast surface display (YSD) approach was utilized to display the hIL17RA-ECD on the yeast cell surface. Schematic representation of yeast surface display of hIL-17RA and detection of expression and binding to hIL-17A is shown in FIG. 2A. The display level of hIL17RA-ECD was monitored using FITC antibody against the c-myc tag at the C-terminal of hIL17RA-ECD. The binding to hIL-17A was monitored by biotynilated α-hIL-17A antibody followed by streptavidin-APC antibody. It was found that the WT hIL17RA-ECD displayed on the yeast surface exhibits very low level of expression and hIL-17A binding (FIG. 2B). Proliferating Cell Nuclear Antigen (PCNA) gene from Saccharomyces cerevisiae expressed under identical conditions (Fridman, Y. et al. PLoS Biol. 2010) was used as a positive control in these experiments (FIG. 2B).

Engineering of hIL17RA-ECD Using Directed Evolution Methodology

To improve the expression level of hIL-17R in E. coli and its affinity for the hIL-17A ligand, a "back to consensus" library was generated by mutating residues in hIL17RA-ECD that deviate from the IL-17RA family consensus back to the family consensus. Based on the alignment summarized in Table 2, 18 relevant positions were identified that deviate from the consensus sequence and mutated these residues by spiking of mutated oligonucleotides to the wild type gene (Herman, A. & Tawfik, D. S. (2007). Incorporating Synthetic Oligonucleotides via Gene Reassembly (ISOR): a versatile tool for generating targeted libraries. Protein Eng Des Sel 20, 219-26.). This naïve "back to consensus" library was transformed to yeast and displayed on the yeast surface (Chao, G. et al. Nat. Protocols 1, 755-768 (2006)).

TABLE 2

Amino Acid Residue Frequency for the hIL17RA-ECD Protein.

| Position[a] | hIL17RA | Mutation[c] |
|---|---|---|
| 10 | L | L10P |
| 15 | P | P15E |
| 44 | D | D44N |
| 45 | L | L45V |
|  |  | L45I |
| 56 | Q | Q56H |
| 60 | F | F60L |
|  |  | F60V |

TABLE 2-continued

Amino Acid Residue Frequency for the hIL17RA-ECD Protein.

| Position[a] | hIL17RA | Mutation[c] |
|---|---|---|
| 97 | R | R97K |
| 109 | R | R109K |
| 123 | D | D123G |
| 156 | H | H156D |
| 157 | A | A157P |
| 240 | R | R240S |
| 244 | G | G244W |
| 249 | Q | Q249H |
| 268 | A | A268V |
| 271 | S | S271P |

Figures 3A, 3B:
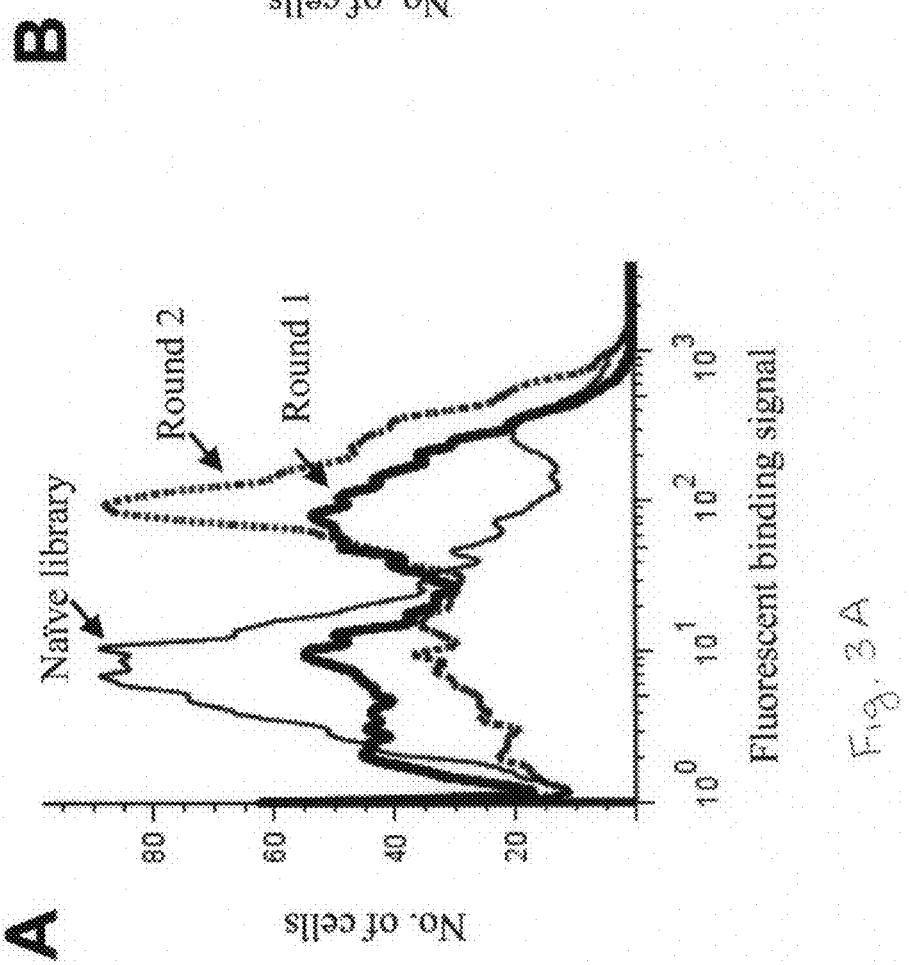
FIG. 3A is a graphical representation of the enrichment process of hIL17RA mutant library displayed on the yeast cell surface using FACS according to the fluorescent expression signal.
FIG. 3B is an additional graphical representation of the enrichment process of hIL17RA mutant library displayed on the yeast cell surface using FACS according to the fluorescent binding signal.

[a]Amino acid residue positions are shown according to the human IL17RA-ECD protein sequence.
[c]Amino acid mutations spiked into hIL17RA-ECD to generate the mutant library To enrich the naïve library for mutants with enhanced expression and affinity for hIL-17A, the library was analyzed and sorted by fluorescence-activated cell sorter (FACS), based on the fluorescence expression and binding signals. Two rounds of enrichment were performed to maintain the active clones and discard the inactive ones (FIGS. 3A, 3B). Next, the enriched libraries were sub-cloned, expressed and screened in E. coli cells for mutants showing enhanced expression level using ELISA. The naïve library was also directly cloned into pET32 plasmid, expressed in E. coli and screened for mutants with higher expression level than that of the WT hIL17R protein. Comparison of the two screening experiments clearly indicates that library enrichment using YSD substantially increased the number of positive clones by a factor of 5 relative to the same library directly screened in E. coli cells without pre-enrichment (see Table 3).

TABLE 3

Comparison Between the Direct Screening of the Naïve Library and Screening of the Same Library Following FACS Enrichment.

| Selection method | No. of screened mutants | No. of improved clones |
|---|---|---|
| ELISA for naive library | 180 | 7 (~4%) |
| ELISA for library after 2 rounds of FACS enrichment | 90 | 16 (~19%) |

Figure 4:
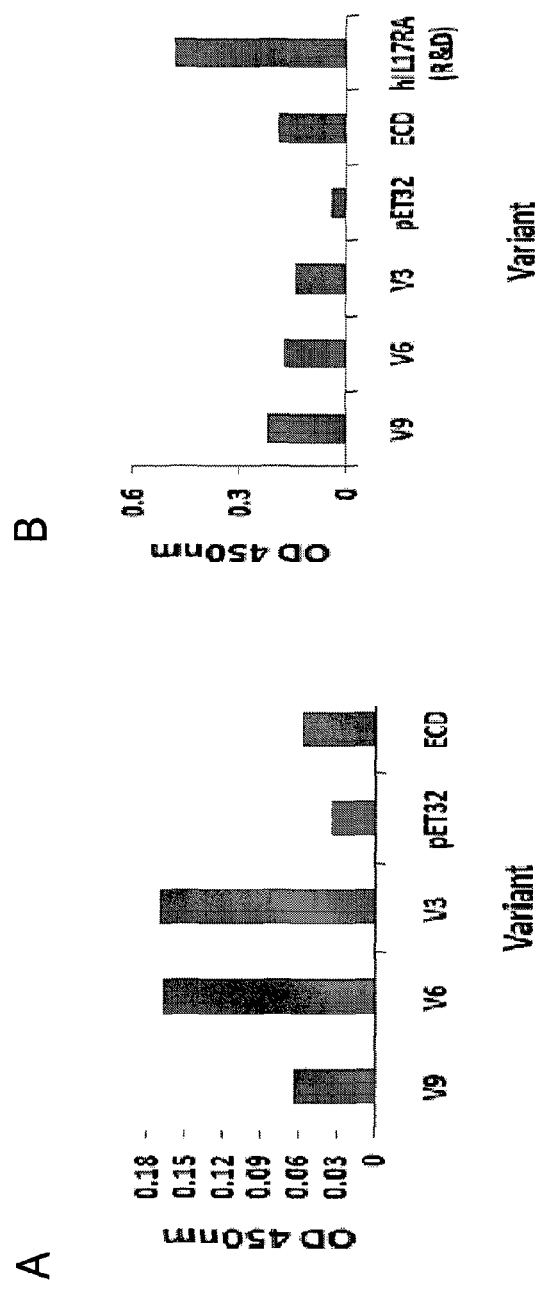
FIG. 4A is a graphical representation of the analysis of the expression level of three IL17RA variants in *E. coli* compared to the WT hIL17RA-ECD and empty vector.
FIG. 4B is an additional graphical representation of the analysis of the binding of three hIL17RA-ECD variants to hIL-17 using ELISA compared to the WT hIL17RA-ECD and empty vector.
Figure 5:
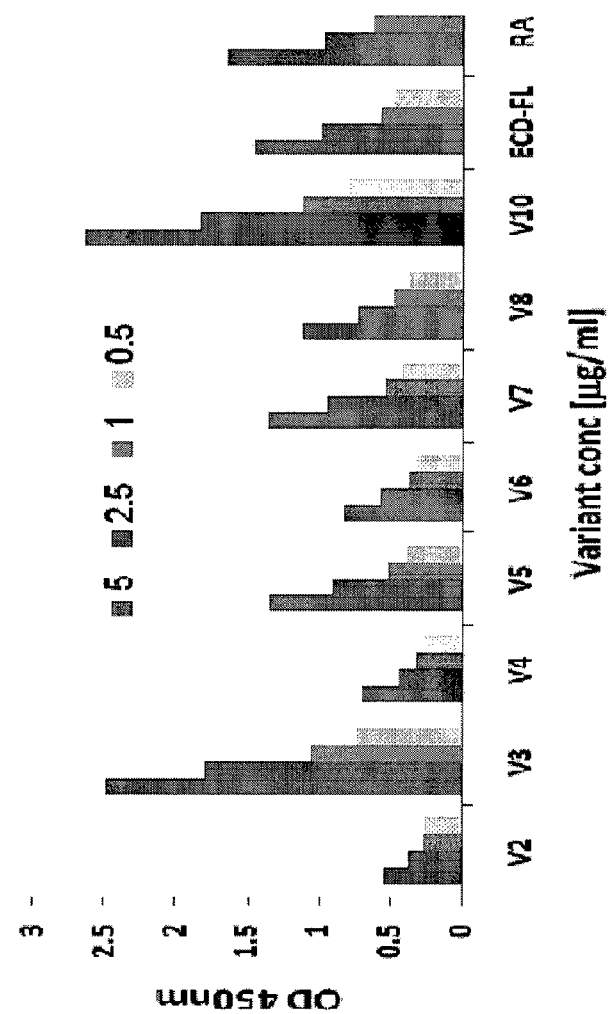
FIG. 5 is a graphical representation of an ELISA experiment for the analysis of binding of eight different hIL17RA-ECD variants (V2-V8 and V10), and the WT hIL17RA-ECD (ECD-FL), expressed in mammalian cells or the commercially available IL17RA-ECD (RA) to hIL-17A immobilization on 96-well plates.

All mutants were screened by both types of ELISA (FIG. 4), for the detection of hIL-17A binding and hIL17RA-ECD expression. Overall, the first round of evolution yielded 22 mutants (Table 4) with higher expression level than that of the WT hIL17RA-ECD (FIG. 4A), but with almost no change in hIL-17A binding affinity (FIG. 4B) relative to the WT IL17RA.

These results indicate that in E. coli cells, these IL17RA mutants are expressed at a higher level than the WT protein (FIG. 4A) but probably due to the lack the natural post translational modification, do not bind efficiently to the IL17A ligand (FIG. 4B).

TABLE 4

List of Mutants of hIL-17RA Obtained in the First Round of Directed Evolution and Selection.

| Number variant | Mutations | | | | | | Number of mutations |
|---|---|---|---|---|---|---|---|
| V1 | P15E | D44N | F60L | R109K | H156D | R240S | 6 |
| V2 | D44N | H156D | | | | | 2 |
| V3 | L10P | R109K | D123G | H156D | G244W | A268V | 6 |
| V4 | L45I | F60L | L69P | H156D | | | 4 |
| V5 | D44N | F60L | R97K | R109K | | | 4 |
| V6 | P15E | F60L | R109K | D123G | | | 4 |
| V7 | F60V | R109K | H156D | | | | 3 |
| V8 | P15E | R109K | H156D | | | | 3 |
| V9 | L10P | P15E | D44N | F60L | R97K | R109K | 6 |
| V10 | L10P | F60V | R109K | D123G | A157P | R109K | 5 |
| V11 | P15E | R109K | Q124R | A157P | | | 4 |
| V12 | L10P | H117R | A157P | | | | 3 |
| V13 | R97K | H156D | N194D | G244W | | | 4 |
| V14 | L45V | Q56H | R109K | G140R | H156D | Q249H | A268V | 7 |
| V15 | L45V | F100I | D123G | A268V | | | 4 |
| V16 | L10P | P15E | R109K | H156D | | | 4 |
| V17 | F60L | K103E | D123G | H156D | | | 4 |
| V18 | N89D | D123G | H156D | | | | 3 |
| V19 | R8Q | P15E | L45I | F60L | | | 4 |
| V20 | L10P | P15E | L45V | F60V | Q124R | A157P | 6 |
| V21 | F60L | R109K | D123G | A157P | E182K | T204I | 6 |
| V22 | F60V | H156D | | | | | 2 |

Expression of Selected hIL17RA Mutants from "Back to Consensus" Library in Mammalian Cells Proteins expressed and purified from *E. coli* lack post-translational modifications that are available in mammalian expression systems (Durocher, Y., Perret, S. & Kamen, A. *Nucleic Acids Research* 30, e9 (2002)), and contain high levels of LPS, a bacterial endotoxin, known to effect mammalian cell line growth and function. The variants V1-V10 were expressed and purified in mammalian cells, similar to the commercially available WT hIL17RA-ECD (Table 4). The produced recombinant proteins were highly pure (>95-98%) and contained low amounts of LPS suitable for testing in human cells (Table 5).

TABLE 5

Analytical Summary of hIL17RA-ECD Variants Produced in Mammalian Cells by CrownBio.

Figure 6:
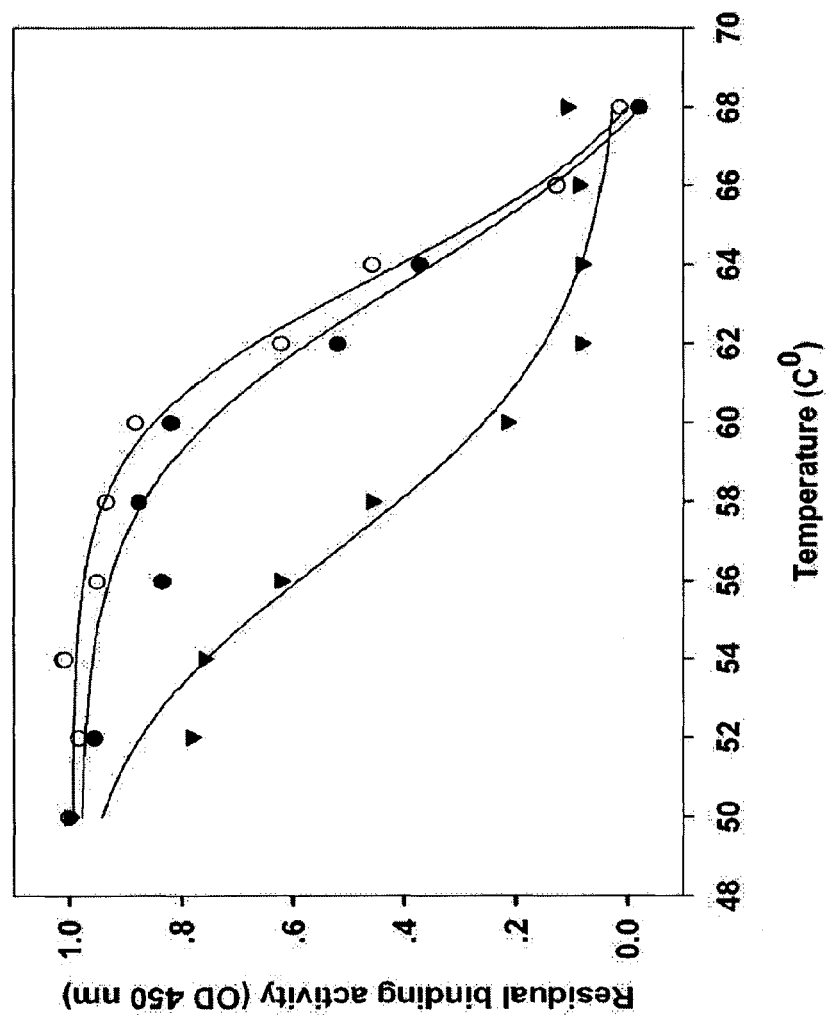
FIG. 6 is a graph showing binding activity of variants V3 (filled circle), V10 empty circle) and hIL17RA-ECD (triangle) following incubation under different temperatures.

| # Variant | Concentration (mg/ml) | Purity by silver stain | Endotoxin (EU/mg) |
|---|---|---|---|
| V1 | 1.6 | >95% | 3.2 |
| V2 | 1.28 | >98% | 2.0 |
| V3 | 1.3 | >98% | 3.4 |
| V4 | 0.97 | >98% | 5.3 |
| V5 | 1.2 | >98% | 2.2 |
| V6 | 1.58 | >98% | 0.8 |
| V7 | 1.8 | >98% | 1.8 |
| V8 | 1.5 | >98% | 0.4 |
| V9 | 1.7 | >98% | 22.9 |
| V10 | 1.0 | >98% | 2.8 |
| ECD-FL | 0.85 | >98% | 5.2 | hIL17A Binding by the hIL17RA-ECD Variants Expressed in Mammalian Cells

To characterize the ability of the different variants purified from mammalian cells to bind hIL-17A, the hIL17RA-hIL-17A interaction was examined by ELISA. The ten variants, V1-V10, and the WT IL17RA-ECD were added at four different concentrations to IL17A pre-coated plates to examine the differences in ELISA signal (FIG. 5). It was found that variants V3 and V10 exhibit higher binding level than the WT hIL17RA-ECD expressed and purified under the same conditions, or the commercially available IL17RA-ECD (FIG. 5).

To quantitatively characterize the differences between the binding affinities of hIL-17A to WT hIL17RA-ECD and to variants V3 and V10, the respective association and dissociation rate constants were measured using surface plasmon resonance (Table 6). It was found that the affinity of the WT hIL17RA-ECD to hIL-17A is 2.6 nM that is in good agreement with the binding affinity previously measured by Wright, J. F. et al. (Wright, J. F. et al. *The Journal of Immunology* 181, 2799-2805 (2008)). Variants V3 and V10 show 6 and 4 fold increased affinity ($K_d$) relative to the WT hIL17RA-ECD, respectively

TABLE 6

Kinetic Rate constants of hIL-17A Cytokine Binding to WT hIL17RA-ECD, V3 and V10 Variants as Determined by SPR.

| Immobilized ligand | $k_a$ (1/M * s) | $k_d$ (1/s) | $K_d$ (M) | Fold increase in affinity |
|---|---|---|---|---|
| WT hIL17RA-ECD | $1.54 \times 10^5$ | $4.04 \times 10^{-4}$ | $2.62 \times 10^{-9} \pm 0.04$ | — |
| V3 | $1.70 \times 10^5$ | $7.51 \times 10^{-5}$ | $4.43 \times 10^{-10} \pm 0.2$ | 6 |
| V10 | $1.84 \times 10^5$ | $1.15 \times 10^{-4}$ | $6.24 \times 10^{-10} \pm 0.15$ | 4.2 |

Temperature Sensitivity of the V3 and V10 Variants

To further characterize the thermostability of the V3 and V10 variants relative to the WT hIL17RA-ECD, the different proteins were incubated for 30 min at different temperatures, ranging from 48° C. to 70° C. The heat inactivated samples were then tested using the ELISA to measure the residual binding activity of each variant to hIL-17A. It was found that the WT IL17RA exhibits no loss in binding signal following incubation at temperatures between 48° C.-50° C. (FIG. 6). However, following incubation of the WT hIL17RA-ECD at ~60° C. a significantly lower residual binding to hIL-17A was observed relative to the same sample incubated at room temperature. In contrast, it was found that both V3 and V10 variants were highly active following incubation at 60° C., indicating a shift of ~5° C. in their heat inactivated temperature compared to the WT hIL17RA-ECD (FIG. 6). Specifically, FIG. 6 shows the thermal inactivation of WT IL-17RA (triangle), V3 (filled circle) and V10 (empty circle) mutants. The IL-17RA variants were incubated at different temperatures for 30 min., and residual IL-17RA binding to IL-17A was monitored at room temperature using ELISA. The results were normalized relative to the variant binding following incubation at 50° C. The heat inactivation temperatures derived from the fits are 57.1±0.6, 63.8±1.2 and 63.9±0.5 for the WT, V3 and V10, respectively. Each data point is the average of two independent experiments.

These results show that the V3 and V10 variants are more thermostable than the WT IL17RA soluble receptor, and thus, exhibit higher stability during long storage periods at room temperature.

Cell Based Assay for IL-6 and Gro-α Secretion

Figure 7:
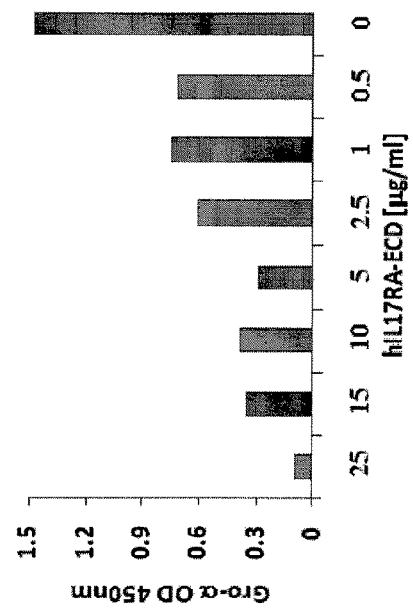
FIG. 7A is a representation of the ability of WT hIL17RA-ECD to inhibit hIL-17A induced secretion of CXCL1 in human fibroblasts.
FIG. 7B is a representation of the ability of WT hIL17RA-ECD to inhibit hIL-17A induced secretion of IL-6 in human fibroblasts.
Figure 7:
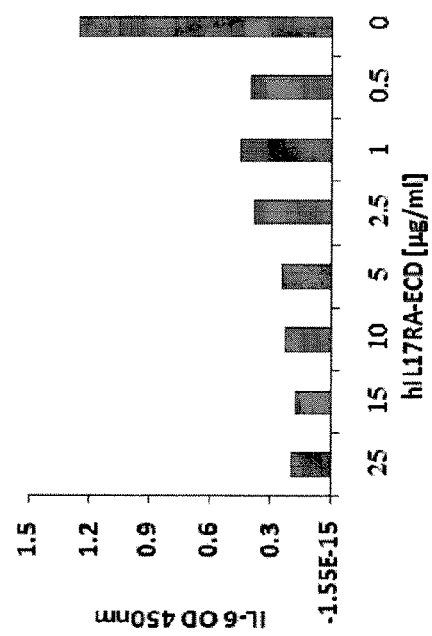

To examine the ability of the recombinant hIL-17RA variants to inhibit hIL-17A binding to fibroblasts, a cell based assay was established. The assay is based on measuring Gro-α and IL-6 secretion following the addition of hIL-17A to the fibroblast cells. The addition of soluble hIL17RA-ECD together with the hIL-17A prevents its binding to the endogenous hIL-17RA receptor, thus leading to reduction in IL-6 and Gro-α secretion. It was found that addition of 0.5 μg/ml commercial hIL17RA-ECD to the fibroblasts together with 10 ng/ml hIL-17A is sufficient to inhibit both Gro-α and IL-6 secretion (FIGS. 7A and 7B respectively) Inhibition of Gro-α was consistent with the inhibition of IL-6 indicating the efficient inhibition of hIL-17A binding to the endogenous receptor.

Figure 8:
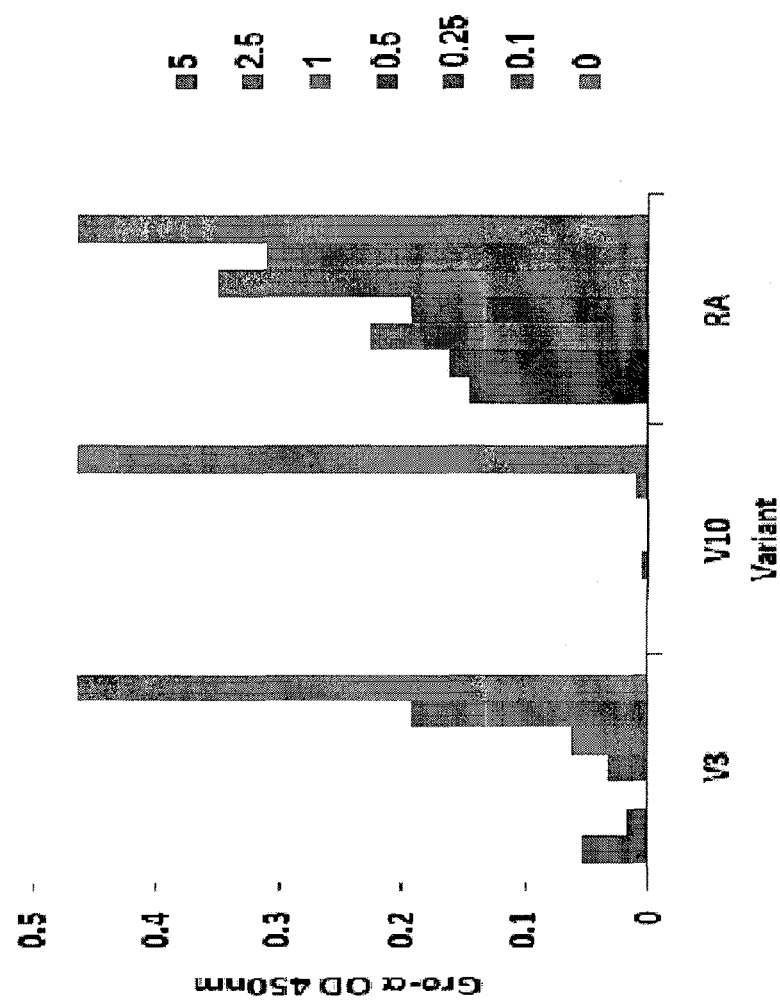
FIG. 8 is a representation of the ability of hIL17RA-ECD, V3 and V10 variants to inhibit hIL-17A induced secretion of CXCL1 in human fibroblasts.

Next, the level of inhibition of IL17 induced secretion of Gro-α following the addition of V3 and V10 variants relative to the soluble WT IL17RA were examined. Both mutants were able to inhibit Gro-α secretion in human fibroblasts at much lower concentrations than the WT protein (FIG. 8). It was found that a significantly lower level of Gro-α is secreted in presence of V3 and V10 at concentrations of 0.25 μg/ml or 0.1 μg/ml relative to the hIL17RA-ECD at the same concentrations.

These results show that the V3 and V10 variants are much more potent in inhibiting the IL17A induced secretion of Gro-α and IL6, and thus, are useful for treating and/or preventing IL17 induced inflammatory disorders.

Example 2

Screening of V10 Random Mutant Library
Error-Prone Library Generation.

Libraries were performed with mutagenic dNTP analogs, 8-oxodG and dPTP, as previously described (Aharoni et al., 2004, Harel et al, 2004).

Figure 9:
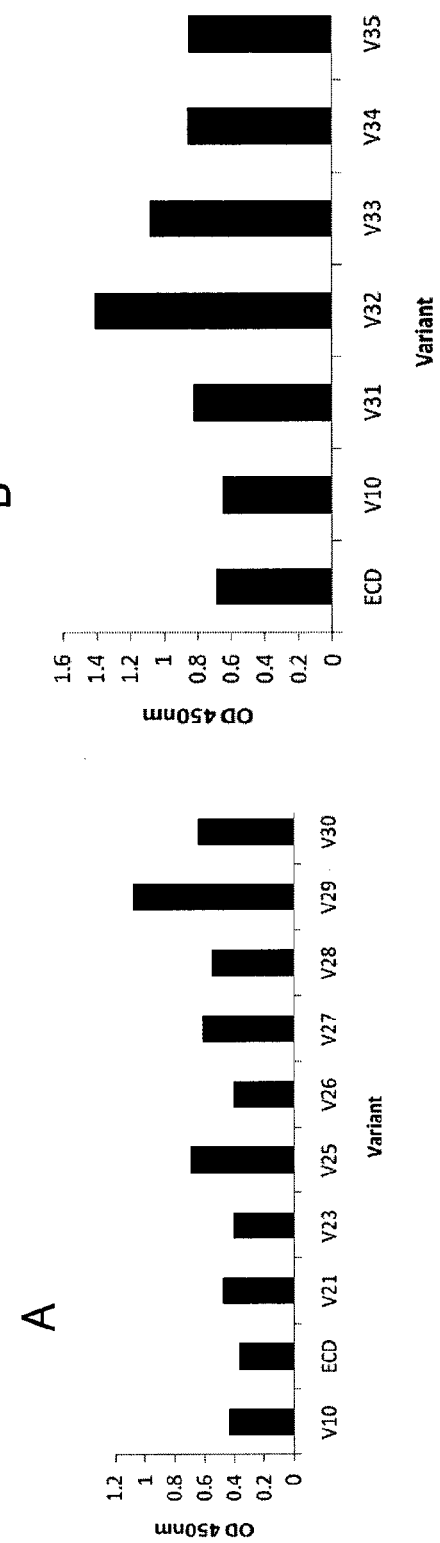
FIGS. 9A and B are representations of ELISA signal of the binding of selected hIL17RA V10 mutants to hIL17A.

Variant V10 isolated from the "back to consensus" library was used as a template for error-prone PCR in order to generate a random mutant library. Individual plasmids containing the V10 mutated gene were isolated from 350 individual colonies following growth in liquid media (Table 7). More than three hundred V10 mutants were then individually transfected, expressed in mammalian cells, and tested for binding to hIL17A using the ELISA for the detection of IL17-IL17R interaction. Eight clones (V23-V30) exhibited similar or higher hIL17A binding than the wt ECD and the original V10 clone expressed under identical conditions (FIG. 9A).

TABLE 7

List of Mutants of V10.

| # variant | Mutations | | | | | | # of mutations |
| --- | --- | --- | --- | --- | --- | --- | --- |
| V23 | F60V | I75T | R109K | D123G | A157P | M209T | 6 |
| V24 | F60V | E79K | R109K | D123G | A157P | I201V | 6 |
| V25 | H53Y | F60V | R109K | D123G | A157P | G244R | 6 |
| V26 | N18S | F60V | L76P | R109K | D123G | A157P | 6 |
| V27 | V21I | F60V | R109K | D123G | A157P | | 5 |
| V28 | N89A | | | | | | 1 |
| V29 | N89A | F190I | | | | | 2 |
| V30 | F60V | R109K | D123G | H131Y | A157P | M209R | 6 |
| V31 | H53Y | F60V | R109K | D123G | A157P | | 5 |
| V32 | F60V | E79K | R109K | D123G | A157P | | 5 |
| V33 | N18S | F60V | N89A | R109K | D123G | A157P | 6 |
| V34 | H33Y | F60V | R109K | D123G | A157P | I201V | 6 |
| V35 | F60V | E79K | R109K | D123G | F113L | A157P | 6 |

Next DNA shuffling between IL17R V23-V30 genes (FIG. 9A) was preformed to generate new IL17R library. More than one hundred individual mutants from the DNA shuffling library were expressed in mammalian cells and analyzed for binding to hIL-17A using the ELISA. Five variants (V31-V35) exhibited higher binding to hIL17A relative to the WT IL17RA ECD or the V10 clone expressed under identical conditions (FIG. 9B).

Example 3

Screening of V10 and V3 Mutant Library

The variants V10N1-V10N8 and V3N2 as presented in table 8 are derived from V10 and V3 respectively with the addition of mutations that were identified in V23-V35 (Table 7) that are beneficial for the stability and or binding and or activity in cell based assay. All these variants are currently generated by CrowBio and expressed in HEK293 to obtain pure protein for subsequent analysis using ELISA and cell based assay.

TABLE 8

List of Mutants of V10 and V3

| # variant | Mutations | | | | | | # of mutations |
|---|---|---|---|---|---|---|---|
| V10N1 | L10P | F60V | R109K | D123G | A157P | N89A | 6 |
| V10N2 | L10P | F60V | R109K | D123G | A157P | E79K | 6 |
| V10N3 | L10P | F60V | R109K | D123G | A157P | H53Y | 6 |
| V10N4 | L10P | F60V | R109K | D123G | A157P | N18S | 6 |
| V10N5 | L10P | F60V | R109K | D123G | A157P | L76P | 6 |
| V10N6 | L10P | F60V | R109K | D123G | A157P | I201V | 6 |
| V10N7 | L10P | F60V | R109K | D123G | A157P | M209T | 6 |
| V10N8 | L10P | F60V | R109K | D123G | A157P | M209R | 6 |
| V3N2 | N89A | R109K | D123G | H156D | | | 4 |

Example 4

The Effect of V3 and V10 on Cytokines Levels

To mimic the effect of IL-17 secreted in, for example, an autoimmune inflammatory disease, IL-17 was injected with or without wt-ECD or one of the ECD-mutants into mice and the levels of various cytokines were measured.

IL-17 (30 µg/mouse) was injected into mice and blood samples for CXCL1 levels assay were collected 2 hrs after the injection.

Figure 10:
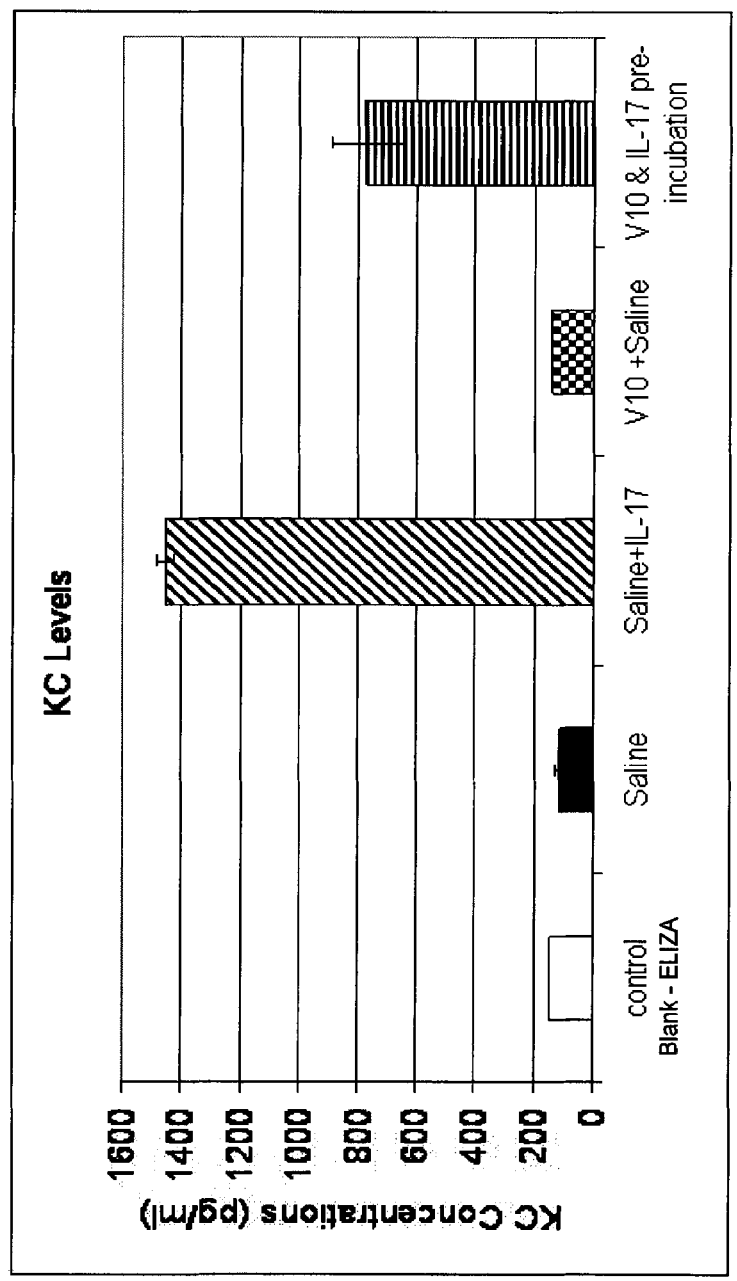
FIG. 10 is a graphical representation of the levels of CXCL1 in response to IL-17 (30 µg/mouse), and V10.

FIG. 10 shows that the levels of CXCL1 cytokine are increased as a result of IL-17 (30 µg/mouse) administration via injection while V10 (14 mg/Kg) mutant did not increase CXCL1 (KC) levels. Furthermore, preincubation of IL-17 with V10 (14 mg/Kg) prior to injection decreased the secreted CXCL1 level by about 40%.

Figure 11:
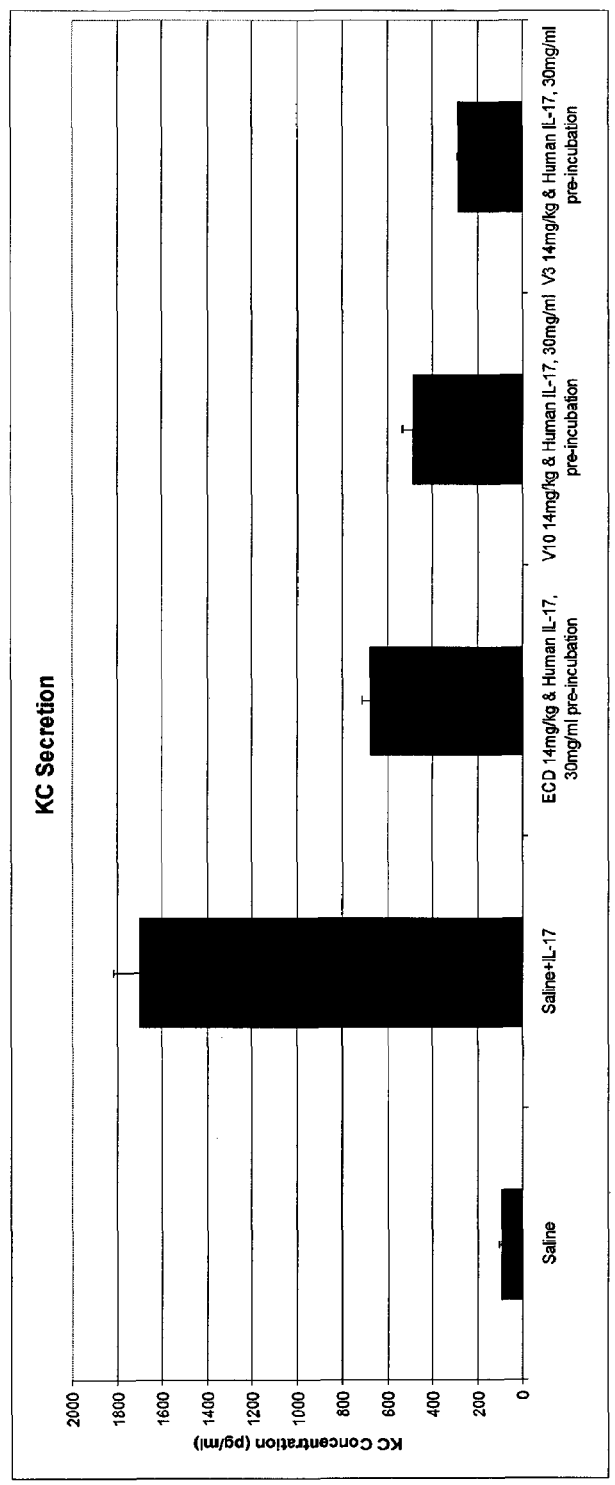
FIG. 11 is a graphical representation of the levels of CXCL1 in response to IL-17 (30 µg/mouse), V3 and V10.

In FIG. 11 shows that the levels of CXCL1 (KC) cytokine are increased as a result of IL-17 (30 µg/mouse) administration via injection pre incubation of the IL-17 with the wt form of the IL-17R (ECD) or the mutants V3 (14 mg/Kg) or V10 (14 mg/Kg) inhibit the secreted levels of CXCL1 (KC) cytokine.

The most potent form is the V3 (14 mg/Kg) inhibits CXCL1 levels by more than 80%. The wt-ECD and V10 (14 mg/Kg) inhibit secreted CXCL1 by 60% and 70%, respectively.

Example 5

Pharmacokinetic Analysis of V3 Variant in Mice

Figure 12:
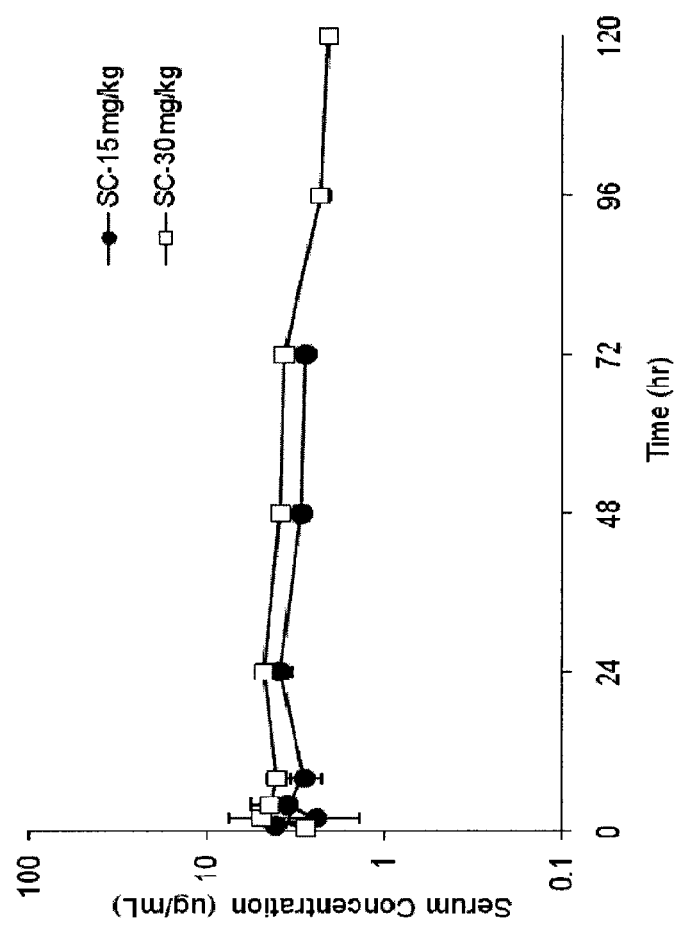
FIG. 12 is a graphical representation of mean serum concentration-time profiles of hIL-17R-V3 after SC dose of 15 and 30 mg/kg in C57BL/6 mice (N=3).

A group of 24 male C57BL/6 mice with a weight of 24-26 g was used for the study. The mice were divided to two groups of 12 mice and the hIL17R-V3 was administered at concentrations of 15 mg/kg or 30 mg/kg via subcutaneous injection (Table 9). The mice had free access to water and food. Blood from the mice was collected at ten different time points following infection. The blood collection was performed following anesthetized under Isoflurane. Approximately 110 µL blood/time point was collected into tube via retro-orbital or cardiac puncture. Blood sample was centrifuged to obtain serum sample (2000 g, 5 min under 4° C.) at room temperature within 30 minutes. The serum samples were stored at −70° C. until analysis by using ELISA. Stability of the V3 in the mice serum was very high with a half life time ($T_{1/2}$) of up to 99.4 hours (Tables 10 and 11). In addition, a high concentration of V3 of up to 4.85 mg/mL in the mice sera was observed (FIG. 12).

The results show high stability of V3 in the sera and the potential of obtaining high concentration of V3 in the sera with few injections over long periods of time.

TABLE 9

Study design of pharmacokinetic study (PK)

| Treatment Group | Treatment | No. of animals | Route of admin. | Dose Level (mg/kg) | Dose Conc. (mg/mL) | Dose Volume (mL/kg) | Time points |
|---|---|---|---|---|---|---|---|
| 1 | hIL-17R-V3 | 12 | SC | 15 | 4.0 | 3.75 | 0.5, 1, 2, 4, 8, 24, 48, 72, 96 & 120 hr, serum collection only |
| 2 | hIL-17R-V3 | 12 | SC | 30 | 4.0 | 7.50 | 0.5, 1, 2, 4, 8, 24, 48, 72, 96 & 120 hr, serum collection only |

TABLE 10

PK results
Individual and mean serum concentration-time data of hIL-17R-V3 after SC dose of 15 mg/kg in C57BL/6 mice[a,b]

| Dose (mg/kg) | Dose Route | Sampling time (hr) | Concentration (µg/mL) Individual | | | Mean (µg/mL) | SD | CV (%) |
|---|---|---|---|---|---|---|---|---|
| 15 | SC | 0.5 | BQL | BQL | BQL | NA | NA | NA |
| | | 1 | 4.35 | 2.94 | 4.90 | 4.06 | 1.01 | 25.0 |
| | | 2 | BQL | 2.43 | 2.35 | 2.39 | 0.0540 | 2.26 |
| | | 4 | 3.38 | 3.02 | 4.13 | 3.51 | 0.569 | 16.2 |
| | | 8 | 2.16 | 3.18 | 3.06 | 2.80 | 0.559 | 19.9 |
| | | 24 | 4.11 | 3.80 | 3.70 | 3.87 | 0.213 | 5.49 |
| | | 48 | 2.98 | 2.86 | 2.99 | 2.94 | 0.076 | 2.59 |
| | | 72 | 2.33 | 2.80 | 3.19 | 2.77 | 0.429 | 15.5 |

TABLE 10-continued

PK results
Individual and mean serum concentration-time data of hIL-17R-V3
after SC dose of 15 mg/kg in C57BL/6 mice[a,b]

|  | 96 | BQL | BQL | BQL | NA | NA | NA |
|---|---|---|---|---|---|---|---|
|  | 120 | BQL | BQL | BQL | NA | NA | NA |

| PK parameters | Unit | Estimated Value |
|---|---|---|
| Tmax | hr | 1.00 |
| Cmax | μg/mL | 4.06 |
| $T_{1/2}$ | hr | 99.4 |
| $AUC_{last}$ | hr * μg/mL | 228 |
| $AUC_{INF}$ | hr * μg/mL | 625 |

[a]BQL: Below Quantifiable Limit of 1.95 μg/mL for hIL-17R-V3 in mouse serum sample
[b]NA: Not Available

TABLE 11

PK results
Individual and mean serum concentration-time data of hIL-17R-V3
after SC dose of 30 mg/kg in C57BL/6 mice[a,b]

| Dose (mg/kg) | Dose Route | Sampling time (hr) | Concentration (μg/mL) Individual | | | Mean (μg/mL) | SD | CV (%) |
|---|---|---|---|---|---|---|---|---|
| 30 | SC | 0.5 | 2.74 | BQL | *11.1 | 2.74 | NA | NA |
|  |  | 1 | BQL | BQL | BQL | NA | NA | NA |
|  |  | 2 | 7.81 | 2.84 | 3.89 | 4.85 | 2.62 | 54.0 |
|  |  | 4 | 3.03 | 5.32 | 4.76 | 4.37 | 1.19 | 27.3 |
|  |  | 8 | 3.55 | 3.74 | 4.68 | 3.99 | 0.604 | 15.1 |
|  |  | 24 | 4.76 | 4.60 | 4.82 | 4.73 | 0.112 | 2.37 |
|  |  | 48 | 3.70 | 4.27 | 3.53 | 3.83 | 0.386 | 10.1 |
|  |  | 72 | 3.24 | 3.88 | 3.77 | 3.63 | 0.344 | 9.49 |
|  |  | 96 | 2.48 | 2.40 | 1.99 | 2.29 | 0.263 | 11.5 |
|  |  | 120 | 2.05 | BQL | BQL | 2.05 | NA | NA |

| PK parameters | Unit | Estimated Value |
|---|---|---|
| Tmax | hr | 2.00 |
| Cmax | μg/mL | 4.85 |
| $T_{1/2}$ | hr | 76.1 |
| $AUC_{last}$ | hr * μg/mL | 417 |
| $AUC_{INF}$ | hr * μg/mL | 642 |

[a]BQL: Below Quantifiable Limit of 1.95 μg/mL for hIL-17R-V3 in mouse serum sample
[b]NA: Not Available Example 6

Contribution of the Different Mutations to IL-17A Activity and Thermostability

To examine the contribution of the back to consensus mutations identified in V3 and V10 to the activity and thermostability of the proteins, a series of site directed mutants were generated and examined. The majority of the mutations found in V3 and V10 individually were mutated back to the WT residue. These mutants were expressed in mammalian cells to maintain posttranslational modifications and examined for binding to IL-17A using ELISA.

The thermostability of the active mutants following 30 min. of incubation at elevated temperatures was examined and characterized by their residual activity using ELISA. Detailed analysis of single mutants of the V3 indicated that two back-to consensus mutations, D123G and H156D were completely essential for IL17-RA binding to IL-17A (Table 12). The results suggest that R109K mutation bring about 50% decrease in binding to IL-17A but significant decrease in thermostability. This analysis also showed that the two mutations, G244W and A268V, that were not part of the back-to consensus mutations and were randomly incorporated during the PCR amplification steps, only slightly contribute to the V3 activity or stability. Similar analysis of mutations in V10M confirmed the importance of D123G and R109K for IL-17A binding and thermostability, respectively. The V10 analysis also revealed that F60V mutation is crucial for IL-17A binding. The mutational analysis indicates that most of the back-to consensus mutations are essential to IL-17RA binding and indicates that these mutations cooperatively contribute to IL-17RA activity. However, this analysis indicated that it was possible to reduce the number of mutations by back mutation of L10P, G244W and A268V thus reducing the number of mutations in V3 from six to three mutations enabling to lower the risk of immunogenicity following administration.

TABLE 12

Mutational analysis of V3 and V10 IL-17RA variants

| IL-17RA variant[a] | Mutations[b] | IL-17A[c] binding relative to the WT | i (° C.)[d] |
|---|---|---|---|
| V3 | L10P, R109K, D123G, H156D, G244W, A268V | 100% | 62 |
| V3 P10L | R109K, D123G, H156D, G244W, A268V | 85% | 62 |
| V3 K109R | L10P, D123G, H156D, G244W, A268V | 45% | 58 |
| V3 G123D | L10P, R109K, H156D, G244W, A268V | <5% | ND |
| V3 D156H | L10P, R109K, D123G, G244W, A268V | <5% | ND |
| V3 W244G | L10P, R109K, D123G, H156D, A268V | 65% | 62 |
| V3M V268A | L10P, R109K, D123G, H156D, G244W | 80% | 62 |
| V10 | L10P, F60V, R109K, D123G, A157P | 100% | 62 |
| V10 V60F | L10P, R109K, D123G, A157P | 10% | ND |
| V10 K109R | L10P, F60V, D123G, A157P | 80% | 58 |
| V10 G123D | L10P, F60V, R109K, A157P | <5% | ND |

[a]IL-17RA variants were expressed in mammalian cells. The back-to-WT mutations in V3 and V10 are highlighted in bold.
[b]List of mutations in each variant following the different back-to-WT mutations
[c]Binding of the UL-17RA mutant was measured by ELISA
[d]Temperature of inactivation determined by the residual binding level following incubation at various temperatures
ND—Not determined.

Example 7

In Vivo Analysis of V3 in Psoriasis Mice Models

Figure 13:
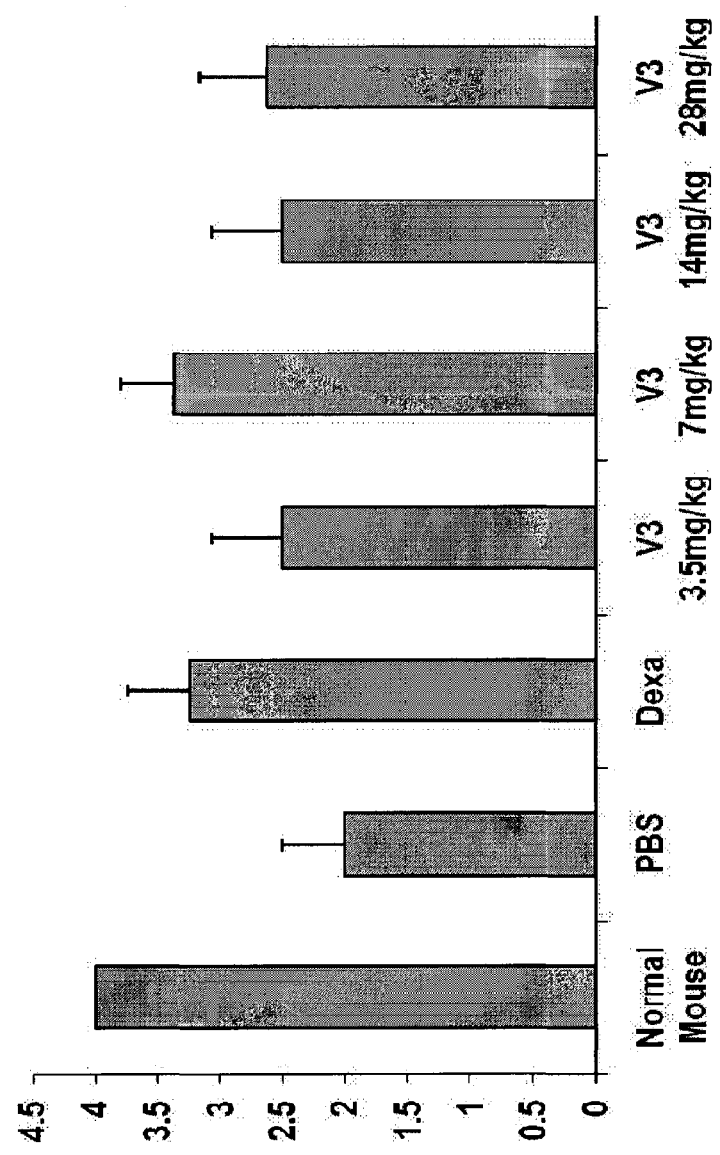
FIG. 13 is a graphical representation of the recovery of psoriasis lesions following administration of V3 IL17R variant at different concentrations.

To assess the therapeutic potential of V3 variant in the recovery of psoriasis lesions, the therapeutic effect of V3 in mice model containing psoriasis lesions was examined. Skin samples from psoriasis patients were transplanted into mice and 28 days following skin transplant V3 was administered via subcutaneous injection twice a week for 4 weeks. Different concentrations of V3 including 3.5 mg/kg, 7 mg/kg, 14 mg/kg and 28 mg/kg were examined. After 56 days from the initial skin transplant the mice were sacrificed and the recovery of the psoriasis lesions was assessed using histology analysis. The level of recovery was scored from 1 to 4 where 1 is sick, 2 is partial recovery, 3 is significant recovery and 4 is a complete recovery (Table 13). As can be seen below (FIG. 13 and Table 13), disease was present in 6/8 of the mice treated with PBS. Treatment with Dexamethasone inhibited disease in 6/8 mice, similar to historical data within this model. sV3R was given to mice at 4 different doses, where the 7 mg/kg significantly inhibited disease in 6/8 mice similar to the effect observed with dexamethasone. Attenuated response at higher V3 concentration was found, probably due to protein aggregation prior administration (FIG. 13).

TABLE 13

Summary of testing of V3 IL17RA in psoriasis mice model

|  | Psoriasis Score 1 | Partial Recovery Score 2 | Partial to Complete Recovery Score 3 | Complete Recovery Score 4 | Avg Score | P Value (vs PBS) |
|---|---|---|---|---|---|---|
| PBS | 5/8 | | 1/8 | 2/8 | 2 ± 0.5 | |
| Dexa | 2/8 | | | 6/8 | 3.25 ± 0.5 | 0.077 |
| V3 3.5 mg/kg | 4/8 | | | 4/8 | 2.5 ± 0.6 | 0.473 |
| V3 7 mg/kg | 1/8 | 1/8 | | 6/8 | 3.4 ± 0.4 | 0.043 |
| V3 14 mg/kg | 4/8 | | | 4/8 | 2.5 ± 0.6 | 0.473 |
| V3 28 mg/kg | 3/8 | 1/8 | | 4/8 | 2.6 ± 0.5 | 0.326 |

It will be appreciated by those skilled in the art to which the present subject matter pertains that various modifications can be made without departing from the essential nature thereof. It is intended to encompass all such modification within the scope of the appended claims.

The invention claimed is:

1. A protein comprising an amino acid sequence having at least 97% homology to SEQ ID NO: 1, wherein said amino acid sequence comprises valine at position 60, glycine at position 123 and lysine at position 109 and wherein said protein binds hIL17A.

2. The protein of claim 1, wherein said protein exhibits increased binding affinity to hIL17A relative to the wild type IL17RA.

3. A protein, comprising the amino acid sequence of SEQ ID NO: 11.

4. An isolated nucleic acid molecule encoding the protein of claim 1.

5. An expression vector comprising the nucleic acid of claim 4.

6. An isolated cell transformed or transfected with the expression vector of claim 5.

7. The cell of claim 6, wherein said cell is a mammalian cell.

8. A pharmaceutical composition, comprising the protein according to claim 1; and a pharmaceutically acceptable carrier or diluent.

9. The pharmaceutical composition of claim 8, formulated in a dosage form selected from the group consisting of an intravenous dosage form and a subcutaneous dosage form.

10. The pharmaceutical composition of claim 8, further comprising at least one anti-inflammatory agent.

11. The pharmaceutical composition of claim 10, wherein said anti-inflammatory agent is selected from the group consisting of: a corticosteroid, cortisol, aldosterone, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, flucinonide, fluocinolone acetonide, halcinonide, betamethasone, betamethasone sodium phosphate, dexamethasone, dexamethasone dodium phosphate, flucortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, flucortolone caproate, fluocortolone pivalate, fluprednidene acetate, a non-steroidal anti-inflammatory, a cox-2 inhibitor, nimesulide, diclofenac, licofelone, aspirin, ibuprofen, naproxen, an immune selective anti-inflammatory derivative, phenylalanine-glutamine-glycine, an herb, Harpagophytum, hyssop, ginger, turmeric, *Arnica Montana*, willow bark, and *cannabis*.

12. A method of treating an inflammatory disorder in a subject in need thereof, comprising administering to the subject a therapeutically effective amount of the pharmaceutical composition of claim 8.

13. The method of claim 12, wherein administering comprises intravenous administration or subcutaneous administration.

14. The method of claim 12, wherein the protein inhibits hIL-17A induced secretion of one or more of IL-6, CXCL1, and TNF-α.

15. A method of treating an inflammatory disorder in a subject in need thereof, comprising administering to the subject a therapeutically effective amount of the protein according to claim 1.

16. The method of claim 15, wherein administering comprises intravenous administration or subcutaneous administration.

17. The method of claim 15, wherein administering further comprises administering a therapeutically effective amount of at least one anti-inflammatory agent.

18. An in vitro method of inhibiting hIL-17A induced secretion of one or more of TNF-α, CXCL1 and IL-6 in a cell, comprising contacting the cell with the protein according to claim 1, in an amount effective to inhibit hIL-17A induced secretion of one or more of TNF-α, IL-6 and CXCL1.

19. The method of claim 18, wherein the cell is a mammalian cell.

20. The method of claim 19, wherein the mammalian cell is a human cell.

* * * * *